(12) United States Patent
Oron et al.

(10) Patent No.: US 11,439,833 B2
(45) Date of Patent: *Sep. 13, 2022

(54) IMPLANT-DELIVERY TOOL

(71) Applicant: BLUEWIND MEDICAL LTD., Herzliya (IL)

(72) Inventors: Gur Oron, Tel Aviv (IL); Bar Eytan, Gedera (IL); Nir Armony, Raanana (IL); Eran Benjamin, Tel Aviv (IL); Jimy Pesin, Haifa (IL)

(73) Assignee: BLUEWIND MEDICAL LTD., Herzlia (IL)

( * ) Notice: Subject to any disclaimer, the term of this patent is extended or adjusted under 35 U.S.C. 154(b) by 15 days.

This patent is subject to a terminal disclaimer.

(21) Appl. No.: 16/934,692

(22) Filed: Jul. 21, 2020

(65) Prior Publication Data
US 2020/0346020 A1 Nov. 5, 2020

Related U.S. Application Data

(63) Continuation of application No. 16/183,783, filed on Nov. 8, 2018, now Pat. No. 10,744,331, which is a
(Continued)

(51) Int. Cl.
*A61N 1/375* (2006.01)
*A61B 17/34* (2006.01)
(Continued)

(52) U.S. Cl.
CPC .......... *A61N 1/375* (2013.01); *A61B 17/3468* (2013.01); *A61N 1/0558* (2013.01); *A61N 1/37205* (2013.01); *A61B 2017/3454* (2013.01)

(58) Field of Classification Search
None
See application file for complete search history.

(56) References Cited

U.S. PATENT DOCUMENTS 3,411,507 A 11/1968 Wingrove
3,693,625 A 9/1972 Auphan
(Continued)

FOREIGN PATENT DOCUMENTS

CN 101048194 10/2007
CN 101500643 8/2009
(Continued)

OTHER PUBLICATIONS

An Office Action dated Dec. 2, 2020, which issued during the prosecution of U.S. Appl. No. 16/166,383.
(Continued)

*Primary Examiner* — Brian T Gedeon
(74) *Attorney, Agent, or Firm* — Sughrue Mion, PLLC

(57) ABSTRACT

Apparatus is provided for facilitating percutaneous delivery of an implant to a target site of a body of a subject. The apparatus includes a delivery tool that includes a needle that defines a lumen through which the implant passes. The needle has a proximal end and a distal end, and defines a triple-grind bevel at the distal end. The triple-grind bevel defines a primary grind and two side-grinds. The side-grinds do not extend to meet each other to define a point at a distal-most part of the needle. Other embodiments are also described.

20 Claims, 12 Drawing Sheets

Related U.S. Application Data continuation of application No. 15/360,501, filed on Nov. 23, 2016, now Pat. No. 10,124,178.

(51) Int. Cl.
  *A61N 1/05* (2006.01)
  *A61N 1/372* (2006.01)

(56) References Cited

U.S. PATENT DOCUMENTS

| | | |
|---|---|---|
| 3,727,616 A | 4/1973 | Lenzkes |
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,036,854 A | 8/1991 | Schollmeyer et al. |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,344,439 A | 9/1994 | Otten |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,071,274 A | 6/2000 | Thompson et al. |
| 6,091,992 A | 6/2000 | Bourgeois |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,496,729 B2 | 12/2002 | Thompson |
| 6,496,730 B1 | 12/2002 | Kleckner et al. |
| 6,582,441 B1 | 6/2003 | He et al. |
| 6,591,139 B2 | 7/2003 | Loftin et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,712,772 B2 | 3/2004 | Cohen et al. |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,770,022 B2 | 8/2004 | Mechlenburg |
| 6,788,973 B2 | 9/2004 | Davis et al. |
| 6,788,975 B1 | 9/2004 | Whitehurst et al. |
| 6,804,561 B2 | 10/2004 | Stover |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 6,950,706 B2 | 9/2005 | Rodriguez et al. |
| 6,993,384 B2 | 1/2006 | Bradley et al. |
| 7,015,769 B2 | 3/2006 | Schulman et al. |
| 7,025,730 B2 | 4/2006 | Cho et al. |
| 7,027,860 B2 | 4/2006 | Bruninga et al. |

(56) References Cited

U.S. PATENT DOCUMENTS

| | | |
|---|---|---|
| 7,047,076 B1 | 5/2006 | Li et al. |
| 7,054,689 B1 | 5/2006 | Whitehurst et al. |
| 7,054,692 B1 | 5/2006 | Whitehurst et al. |
| 7,070,583 B1 * | 7/2006 | Higuchi ............... A61M 5/3286 604/274 |
| 7,110,820 B2 | 9/2006 | Tcheng et al. |
| 7,149,575 B2 | 12/2006 | Ostroff et al. |
| 7,151,914 B2 | 12/2006 | Brewer |
| 7,174,218 B1 | 2/2007 | Kuzma |
| 7,177,690 B2 | 2/2007 | Woods et al. |
| 7,177,698 B2 | 2/2007 | Klosterman et al. |
| 7,190,998 B2 | 3/2007 | Shalev et al. |
| 7,203,549 B2 | 4/2007 | Schommer et al. |
| 7,209,792 B1 | 4/2007 | Parramon et al. |
| 7,212,867 B2 | 5/2007 | Venrooij et al. |
| 7,216,000 B2 | 5/2007 | Sieracki et al. |
| 7,225,032 B2 | 5/2007 | Schmeling et al. |
| 7,228,178 B2 | 6/2007 | Carroll |
| 7,239,921 B2 | 7/2007 | Canfield et al. |
| 7,242,982 B2 | 7/2007 | Singhal et al. |
| 7,254,449 B2 | 8/2007 | Karunasiri |
| 7,263,402 B2 | 8/2007 | Thacker et al. |
| 7,277,748 B2 | 10/2007 | Wingeier et al. |
| 7,277,749 B2 | 10/2007 | Gordon et al. |
| 7,286,880 B2 | 10/2007 | Olson et al. |
| 7,286,881 B2 | 10/2007 | Schommer et al. |
| 7,289,853 B1 | 10/2007 | Campbell et al. |
| 7,292,890 B2 | 11/2007 | Whitehurst et al. |
| 7,308,316 B2 | 12/2007 | Schommer |
| 7,324,852 B2 | 1/2008 | Barolat et al. |
| 7,324,853 B2 | 1/2008 | Ayal |
| 7,330,756 B2 | 2/2008 | Marnfeldt |
| 7,337,007 B2 | 2/2008 | Nathan et al. |
| 7,342,508 B2 | 3/2008 | Morgan et al. |
| 7,363,087 B2 | 4/2008 | Nghiem et al. |
| 7,376,466 B2 | 5/2008 | He et al. |
| 7,389,145 B2 | 6/2008 | Kilgore et al. |
| 7,483,748 B2 | 1/2009 | Torgerson et al. |
| 7,483,752 B2 | 1/2009 | Von arx et al. |
| 7,489,561 B2 | 2/2009 | Armstrong et al. |
| 7,502,652 B2 | 3/2009 | Gaunt et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,536,226 B2 | 5/2009 | Williams |
| 7,539,538 B2 | 5/2009 | Parramon et al. |
| 7,561,921 B2 | 7/2009 | Phillips et al. |
| 7,565,204 B2 | 7/2009 | Matei |
| 7,628,750 B2 | 12/2009 | Cohen |
| 7,630,771 B2 | 12/2009 | Cauller |
| 7,634,313 B1 | 12/2009 | Kroll et al. |
| 7,643,147 B2 | 1/2010 | Pless |
| 7,647,117 B2 | 1/2010 | Bauhahn |
| 7,650,192 B2 | 1/2010 | Wahlstrand |
| 7,655,014 B2 | 2/2010 | Ko et al. |
| 7,657,311 B2 | 2/2010 | Bardy et al. |
| 7,657,317 B2 | 2/2010 | Thacker et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,680,540 B2 | 3/2010 | Jensen et al. |
| 7,711,434 B2 | 5/2010 | Denker et al. |
| 7,736,379 B2 | 6/2010 | Ewers et al. |
| 7,747,325 B2 | 6/2010 | Dilorenzo |
| 7,780,625 B2 | 8/2010 | Bardy |
| 7,797,050 B2 | 9/2010 | Libbus et al. |
| 7,801,602 B2 | 9/2010 | McClure et al. |
| 7,803,142 B2 | 9/2010 | Longson et al. |
| 7,809,437 B2 | 10/2010 | Palmer et al. |
| 7,817,280 B2 | 10/2010 | Pless |
| 7,822,480 B2 | 10/2010 | Park et al. |
| 7,848,818 B2 | 12/2010 | Barolat et al. |
| 7,869,867 B2 | 1/2011 | Armstrong et al. |
| 7,894,905 B2 | 2/2011 | Pless et al. |
| 7,899,547 B1 | 3/2011 | Emadi et al. |
| 7,899,556 B2 | 3/2011 | Nathan et al. |
| 7,904,171 B2 | 3/2011 | Parramon et al. |
| 7,912,551 B2 | 3/2011 | Wosmek |
| 7,925,350 B1 | 4/2011 | Palmer |
| 7,917,226 B2 | 5/2011 | Nghiem |
| 7,937,148 B2 | 5/2011 | Jacobson |
| 7,941,218 B2 | 5/2011 | Sambelashvili et al. |
| 7,962,211 B2 | 6/2011 | Torgerson et al. |
| 7,962,220 B2 | 6/2011 | Kolafa et al. |
| 7,974,706 B2 | 7/2011 | Moffitt et al. |
| 7,979,126 B2 | 7/2011 | Payne et al. |
| 7,991,467 B2 | 8/2011 | Markowitz et al. |
| 7,996,079 B2 | 8/2011 | Armstrong |
| 7,996,089 B2 | 8/2011 | Haugland et al. |
| 7,996,092 B2 | 8/2011 | Mrva et al. |
| 8,005,547 B2 | 8/2011 | Forsberg et al. |
| 8,019,443 B2 | 9/2011 | Scheicher et al. |
| 8,050,771 B2 | 11/2011 | Yamamoto et al. |
| 8,055,336 B1 | 11/2011 | Schulman et al. |
| 8,055,350 B2 | 11/2011 | Roberts |
| 8,075,556 B2 | 12/2011 | Betts |
| 8,086,313 B2 | 12/2011 | Singhal et al. |
| 8,090,438 B2 | 1/2012 | Bardy et al. |
| 8,115,448 B2 | 2/2012 | John |
| 8,127,424 B2 | 3/2012 | Haller et al. |
| 8,131,377 B2 | 3/2012 | Shhi et al. |
| 8,140,168 B2 | 3/2012 | Olson et al. |
| 8,170,675 B2 | 5/2012 | Alataris et al. |
| 8,170,681 B2 | 5/2012 | Jimenez et al. |
| 8,175,719 B2 | 5/2012 | Shi et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,229,567 B2 | 7/2012 | Phillips et al. |
| 8,244,367 B2 | 8/2012 | Wahlstrand et al. |
| 8,255,057 B2 | 8/2012 | Fang et al. |
| 8,260,432 B2 | 9/2012 | DiGiore et al. |
| 8,265,770 B2 | 9/2012 | Toy et al. |
| 8,306,627 B2 | 11/2012 | Armstrong |
| 8,311,638 B2 | 11/2012 | Aghassian |
| 8,321,028 B1 | 11/2012 | Thenuwara et al. |
| 8,335,569 B2 | 12/2012 | Aghassian |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,267 B2 | 1/2013 | Schleicher et al. |
| 8,369,963 B2 | 2/2013 | Parramon et al. |
| 8,374,700 B2 | 2/2013 | Haubrich et al. |
| 8,386,047 B2 | 2/2013 | Koester |
| 8,386,048 B2 | 2/2013 | McClure et al. |
| 8,396,559 B2 | 3/2013 | Alataris et al. |
| 8,428,731 B2 | 4/2013 | Armstrong |
| 8,428,744 B2 | 4/2013 | Stancer et al. |
| 8,428,746 B2 | 4/2013 | Digiore et al. |
| 8,428,748 B2 | 4/2013 | Alataris et al. |
| 8,437,846 B2 | 5/2013 | Swoyer et al. |
| 8,437,853 B2 | 5/2013 | Inman et al. |
| 8,457,744 B2 | 6/2013 | Janzig et al. |
| 8,457,759 B2 | 6/2013 | Parker et al. |
| 8,463,404 B2 | 6/2013 | Levi et al. |
| 8,473,066 B2 | 6/2013 | Aghassian et al. |
| 8,478,420 B2 | 7/2013 | Armstrong et al. |
| 8,483,838 B2 | 7/2013 | Nghiem et al. |
| 8,483,845 B2 | 7/2013 | Sage |
| 8,494,640 B2 | 7/2013 | Peterson et al. |
| 8,494,650 B2 | 7/2013 | Glukhovsky et al. |
| 8,497,804 B2 | 7/2013 | Haubrich et al. |
| 8,498,716 B2 | 7/2013 | Chen et al. |
| 8,509,905 B2 | 8/2013 | Alataris et al. |
| 8,509,906 B2 | 8/2013 | Walker et al. |
| 8,515,558 B1 | 8/2013 | Zweber et al. |
| 8,538,548 B2 | 9/2013 | Shi et al. |
| 8,543,200 B2 | 9/2013 | Lane et al. |
| 8,554,326 B2 | 10/2013 | Alataris et al. |
| 8,555,894 B2 | 10/2013 | Schulman et al. |
| 8,571,651 B2 | 10/2013 | Ben-ezra et al. |
| 8,577,474 B2 | 11/2013 | Rahman et al. |
| 8,588,933 B2 | 11/2013 | Floyd et al. |

(56) References Cited

U.S. PATENT DOCUMENTS

| | | |
|---|---|---|
| 8,612,014 B2 | 12/2013 | Rahman et al. |
| 8,612,019 B2 | 12/2013 | Moffitt |
| 8,620,435 B2 | 12/2013 | Rooney et al. |
| 8,620,449 B2 | 12/2013 | Zhao et al. |
| 8,626,310 B2 | 1/2014 | Barror et al. |
| 8,634,927 B2 | 1/2014 | Olson et al. |
| 8,644,947 B2 | 2/2014 | Zhu et al. |
| 8,644,948 B2 | 2/2014 | Grevious et al. |
| 8,649,874 B2 | 2/2014 | Alataris et al. |
| 8,660,655 B2 | 2/2014 | Peterson et al. |
| 8,666,491 B2 | 3/2014 | Chen et al. |
| 8,666,504 B2 | 3/2014 | Dronov et al. |
| 8,676,337 B2 | 3/2014 | Kallmyer |
| 8,676,341 B2 | 3/2014 | Kane et al. |
| 8,688,232 B2 | 4/2014 | Finley et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,780 B2 | 5/2014 | Lee |
| 8,718,781 B2 | 5/2014 | Alataris et al. |
| 8,718,782 B2 | 5/2014 | Alataris et al. |
| 8,738,145 B2 | 5/2014 | Goetz et al. |
| 8,750,985 B2 | 6/2014 | Parramon et al. |
| 8,751,009 B2 | 6/2014 | Wacnik |
| 8,755,893 B2 | 6/2014 | Gross et al. |
| 8,761,895 B2 | 6/2014 | Stevenson et al. |
| 8,768,472 B2 | 7/2014 | Fang et al. |
| 8,774,912 B2 | 7/2014 | Gerber |
| 8,774,926 B2 | 7/2014 | Alataris et al. |
| 8,788,045 B2 | 7/2014 | Gross et al. |
| 8,792,988 B2 | 7/2014 | Alataris et al. |
| 8,798,773 B2 | 8/2014 | Mashiach |
| 8,805,519 B2 | 8/2014 | Parker et al. |
| 8,812,135 B2 | 8/2014 | Mashiach |
| 8,843,203 B2 | 9/2014 | Lee et al. |
| 8,849,410 B2 | 9/2014 | Walker et al. |
| 8,849,412 B2 | 9/2014 | Perryman et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,219 B2 | 10/2014 | Trier et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,884,779 B2 | 11/2014 | Herman et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,892,214 B2 | 11/2014 | Bonde et al. |
| 8,903,497 B2 | 12/2014 | Norgaard et al. |
| 8,903,499 B2 | 12/2014 | Pless et al. |
| 8,918,179 B2 | 12/2014 | Peterson et al. |
| 8,918,180 B2 | 12/2014 | Peterson |
| 8,923,988 B2 | 12/2014 | Bradley |
| 8,942,808 B2 | 1/2015 | Peterson et al. |
| 8,954,165 B2 | 2/2015 | Sharma et al. |
| 8,958,884 B2 | 2/2015 | Kothandaraman et al. |
| 8,958,891 B2 | 2/2015 | Kane et al. |
| 8,983,615 B2 | 3/2015 | Tahmasian et al. |
| 8,983,618 B2 | 3/2015 | Yamamoto et al. |
| 8,989,864 B2 | 3/2015 | Funderburk et al. |
| 8,989,868 B2 | 3/2015 | Mashiach et al. |
| 8,994,325 B2 | 3/2015 | Carbunaru et al. |
| 8,996,115 B2 | 3/2015 | Trier et al. |
| 9,002,445 B2 | 4/2015 | Chen |
| 9,002,460 B2 | 4/2015 | Parker |
| 9,002,461 B2 | 4/2015 | Walker et al. |
| 9,002,466 B2 | 4/2015 | Trier et al. |
| 9,020,599 B2 | 4/2015 | Rooney et al. |
| 9,020,602 B2 | 4/2015 | Aghassian |
| 9,026,227 B2 | 5/2015 | Daglow |
| 9,030,159 B2 | 5/2015 | Chen et al. |
| 9,031,666 B2 | 5/2015 | Fell |
| 9,037,261 B2 | 5/2015 | Bradley |
| 9,042,997 B2 | 5/2015 | Rahman et al. |
| 9,044,616 B2 | 6/2015 | Chen et al. |
| 9,056,206 B2 | 6/2015 | Torgerson et al. |
| 9,061,140 B2 | 6/2015 | Shi et al. |
| 9,061,151 B2 | 6/2015 | Mashiach et al. |
| 9,061,159 B2 | 6/2015 | Rahman |
| 9,061,162 B2 | 6/2015 | Mashiach et al. |
| 9,067,072 B2 | 6/2015 | Tahmasian et al. |
| 9,070,507 B2 | 6/2015 | Dronov et al. |
| 9,072,896 B2 | 7/2015 | Dar et al. |
| 9,079,041 B2 | 7/2015 | Park et al. |
| 9,084,900 B2 | 7/2015 | Hershey et al. |
| 9,089,712 B2 | 7/2015 | Joshi et al. |
| 9,095,726 B2 | 8/2015 | Parramon et al. |
| 9,101,774 B2 | 8/2015 | Mashiach et al. |
| 9,119,969 B2 | 9/2015 | Vansickle |
| 9,142,989 B2 | 9/2015 | Fell et al. |
| 9,149,635 B2 | 10/2015 | Denison et al. |
| 9,149,643 B2 | 10/2015 | Tahmasian et al. |
| 9,154,219 B2 | 10/2015 | Polefko et al. |
| 9,155,899 B2 | 10/2015 | Mashiach et al. |
| 9,155,901 B2 | 10/2015 | Dearden et al. |
| 9,162,068 B2 | 10/2015 | Dronov |
| 9,174,051 B2 | 11/2015 | Marnfeldt et al. |
| 9,174,053 B2 | 11/2015 | Zhu |
| 9,186,504 B2 | 11/2015 | Gross |
| 9,192,770 B2 | 11/2015 | Wang et al. |
| 9,199,083 B2 | 12/2015 | Caparso et al. |
| 9,205,258 B2 | 12/2015 | Simon et al. |
| 9,211,418 B2 | 12/2015 | Aghassian |
| 9,216,297 B2 | 12/2015 | Kast et al. |
| 9,220,907 B2 | 12/2015 | Mashiach et al. |
| 9,220,909 B2 | 12/2015 | Carbunaru et al. |
| 9,220,910 B2 | 12/2015 | Colborn |
| 9,225,194 B2 | 12/2015 | Joshi |
| 9,227,075 B2 | 1/2016 | Aghassian et al. |
| 9,232,903 B2 | 1/2016 | Pless et al. |
| 9,238,138 B2 | 1/2016 | Lee et al. |
| 9,240,630 B2 | 1/2016 | Joshi |
| 9,242,106 B2 | 1/2016 | Klosterman et al. |
| 9,248,279 B2 | 2/2016 | Chen et al. |
| 9,248,292 B2 | 2/2016 | Trier et al. |
| 9,248,302 B2 | 2/2016 | Mashiach et al. |
| 9,254,393 B2 | 2/2016 | Perryman et al. |
| 9,259,571 B2 | 2/2016 | Straka et al. |
| 9,259,582 B2 | 2/2016 | Joshi et al. |
| 9,259,584 B2 | 2/2016 | Bauhahn et al. |
| 9,265,941 B2 | 2/2016 | Van Den Biggelaar et al. |
| 9,265,958 B2 | 2/2016 | Joshi et al. |
| 9,289,616 B2 | 3/2016 | Koester |
| 9,295,841 B2 | 3/2016 | Fang et al. |
| 9,295,850 B2 | 3/2016 | Kallmyer |
| 9,314,613 B2 | 4/2016 | Mashiach |
| 9,314,628 B2 | 4/2016 | North et al. |
| 9,314,642 B2 | 4/2016 | Ozawa et al. |
| 9,320,847 B2 | 4/2016 | Rooney et al. |
| 9,320,899 B2 | 4/2016 | Parramon et al. |
| 9,320,908 B2 | 4/2016 | Fletcher et al. |
| 9,333,367 B2 | 5/2016 | Chen |
| 9,339,660 B2 | 5/2016 | Feldman et al. |
| 9,343,923 B2 | 5/2016 | Joshi |
| 9,352,161 B2 | 5/2016 | Thacker et al. |
| 9,370,664 B2 | 6/2016 | Marnfeldt et al. |
| 9,375,582 B2 | 6/2016 | Kaula et al. |
| 9,381,360 B2 | 7/2016 | Hershey |
| 9,387,331 B2 | 7/2016 | Zhao et al. |
| 9,387,332 B2 | 7/2016 | Zhao et al. |
| 9,393,423 B2 | 7/2016 | Parramon et al. |
| 9,393,428 B2 | 7/2016 | Nyberg, II et al. |
| 9,393,435 B2 | 7/2016 | Mashiach |
| 9,398,901 B2 | 7/2016 | Tischendorf et al. |
| 9,399,130 B2 | 7/2016 | Bonde et al. |
| 9,399,131 B2 | 7/2016 | Digiore et al. |
| 9,399,143 B2 | 7/2016 | Yamamoto et al. |
| 9,403,013 B2 | 8/2016 | Walker et al. |
| 9,403,020 B2 | 8/2016 | Wingeier |
| 9,403,021 B2 | 8/2016 | Dronov |
| 9,407,110 B2 | 8/2016 | Lui et al. |

(56) References Cited

U.S. PATENT DOCUMENTS

| | | |
|---|---|---|
| 9,409,029 B2 | 8/2016 | Perryman et al. |
| 9,435,830 B2 | 9/2016 | Joshi |
| 9,446,251 B1 | 9/2016 | Perryman et al. |
| 9,446,254 B2 | 9/2016 | Ozawa et al. |
| 9,449,501 B2 | 9/2016 | Grevious et al. |
| 9,452,288 B2 | 9/2016 | Whitehurst et al. |
| 9,457,186 B2 | 10/2016 | Gross |
| 9,463,321 B2 | 10/2016 | Bradley et al. |
| 9,463,323 B2 | 10/2016 | Lee et al. |
| 9,463,326 B2 | 10/2016 | Ranu |
| 9,468,771 B2 | 10/2016 | Griffith et al. |
| 9,468,772 B2 | 10/2016 | Demmer |
| 9,469,437 B2 | 10/2016 | Kamath |
| 9,474,905 B2 | 10/2016 | Doan et al. |
| 9,480,841 B2 | 11/2016 | Hershey et al. |
| 9,504,832 B2 | 11/2016 | Libbus et al. |
| 9,504,838 B2 | 11/2016 | Rao et al. |
| 9,517,344 B1 | 12/2016 | Bradley |
| 9,517,352 B2 | 12/2016 | Kast et al. |
| 9,522,270 B2 | 12/2016 | Perryman et al. |
| 9,533,148 B2 | 1/2017 | Carcieri |
| 9,533,153 B2 | 1/2017 | Libbus et al. |
| 9,533,154 B2 | 1/2017 | Kothandaraman et al. |
| 9,533,162 B2 | 1/2017 | Ter-petrosyan et al. |
| 9,555,257 B2 | 1/2017 | Mashiach et al. |
| 9,561,365 B2 | 2/2017 | Shi et al. |
| 9,585,642 B2 | 3/2017 | Dinsmoor et al. |
| 9,586,054 B2 | 3/2017 | Aghassian |
| 9,592,385 B2 | 3/2017 | Kaula et al. |
| 9,597,516 B2 | 3/2017 | Lee et al. |
| 9,597,517 B2 | 3/2017 | Moffitt |
| 9,597,521 B2 | 3/2017 | Plotkin et al. |
| 9,610,450 B2 | 4/2017 | Zhao |
| 9,616,230 B2 | 4/2017 | Grandhe |
| 9,623,244 B2 | 4/2017 | Kothandaraman |
| 9,623,245 B2 | 4/2017 | King et al. |
| 9,623,253 B2 | 4/2017 | Perryman et al. |
| 9,623,257 B2 | 4/2017 | Olson et al. |
| 9,630,231 B2 | 4/2017 | Kelsch et al. |
| 9,636,508 B2 | 5/2017 | Chen et al. |
| 9,643,022 B2 | 5/2017 | Mashiach et al. |
| 9,649,049 B2 | 5/2017 | Pless et al. |
| 9,649,493 B2 | 5/2017 | Mashiach |
| 9,653,941 B2 | 5/2017 | Dinsmoor et al. |
| 9,656,074 B2 | 5/2017 | Simon et al. |
| 9,656,076 B2 | 5/2017 | Trier et al. |
| 9,656,081 B2 | 5/2017 | Feldman et al. |
| 9,675,809 B2 | 6/2017 | Chow |
| 9,687,649 B2 | 6/2017 | Thacker |
| 9,700,725 B2 | 7/2017 | Zhu |
| 9,700,730 B2 | 7/2017 | Carbunaru et al. |
| 9,707,404 B2 | 7/2017 | Rao et al. |
| 9,713,707 B2 | 7/2017 | Oron et al. |
| 9,713,717 B2 | 7/2017 | Aghassian |
| 9,713,718 B2 | 7/2017 | Lamont et al. |
| 9,713,721 B2 | 7/2017 | Kothandaraman |
| 9,724,513 B2 | 8/2017 | Lane et al. |
| 9,731,116 B2 | 8/2017 | Chen |
| 9,737,703 B2 | 8/2017 | Carbunaru et al. |
| 9,737,714 B2 | 8/2017 | Zottola |
| 9,744,347 B2 | 8/2017 | Chen et al. |
| 9,744,362 B2 | 8/2017 | Steinke et al. |
| 9,744,365 B2 | 8/2017 | Davis et al. |
| 9,744,368 B2 | 8/2017 | Dinsmoor |
| 9,750,930 B2 | 9/2017 | Chen |
| 9,782,588 B2 | 10/2017 | Shi et al. |
| 9,782,593 B2 | 10/2017 | Parramon et al. |
| 9,782,596 B2 | 10/2017 | Vamos et al. |
| 9,789,314 B2 | 10/2017 | Perryman et al. |
| 9,789,321 B2 | 10/2017 | Dixit et al. |
| 9,789,324 B2 | 10/2017 | Bauhahn et al. |
| 9,802,038 B2 | 10/2017 | Lee et al. |
| 9,802,048 B2 | 10/2017 | Armstrong |
| 9,802,052 B2 | 10/2017 | Marnfeldt |
| 9,814,458 B2 | 11/2017 | North |
| 9,814,880 B2 | 11/2017 | Hershey et al. |
| 9,814,884 B2 | 11/2017 | Parker et al. |
| 9,839,786 B2 | 12/2017 | Rondoni et al. |
| 9,844,677 B2 | 12/2017 | Aghassian |
| 9,849,298 B2 | 12/2017 | Ozawa et al. |
| 9,855,436 B2 | 1/2018 | Dearden et al. |
| 9,861,812 B2 | 1/2018 | Gross et al. |
| 9,861,825 B2 | 1/2018 | Ozawa et al. |
| 9,867,989 B2 | 1/2018 | Blum et al. |
| 9,867,994 B2 | 1/2018 | Parramon |
| 9,878,158 B2 | 1/2018 | Hershey et al. |
| 9,913,980 B2 | 3/2018 | Ostroff et al. |
| 9,913,986 B2 | 3/2018 | Chow et al. |
| 9,913,990 B2 | 3/2018 | Ter-Petrosyan et al. |
| 9,925,381 B2 | 3/2018 | Nassif |
| 9,929,584 B2 | 3/2018 | Aghassian et al. |
| 9,931,107 B2 | 4/2018 | Tischendorf et al. |
| 9,935,498 B2 | 4/2018 | Joshi |
| 9,943,685 B2 | 4/2018 | Ramesh et al. |
| 9,950,166 B2 | 4/2018 | Mashiach et al. |
| 9,950,173 B2 | 4/2018 | Doan |
| 9,950,179 B2 | 4/2018 | Bonde et al. |
| 9,956,419 B2 | 5/2018 | Bokil |
| 9,956,421 B2 | 5/2018 | Bunyan et al. |
| 9,974,965 B2 | 5/2018 | Perryman et al. |
| 9,981,130 B2 | 5/2018 | Lee |
| 9,993,645 B2 | 6/2018 | Walker et al. |
| 10,004,896 B2 | 6/2018 | Oron et al. |
| 10,010,717 B2 | 7/2018 | Aghassian et al. |
| 10,014,571 B2 | 7/2018 | Andersen et al. |
| 10,056,688 B2 | 8/2018 | Andersen et al. |
| 10,058,705 B2 | 8/2018 | Andersen et al. |
| 10,064,288 B2 | 8/2018 | Li et al. |
| 10,080,902 B2 | 9/2018 | Dinsmoor et al. |
| 10,105,540 B2 | 10/2018 | Oron et al. |
| 10,105,542 B2 | 10/2018 | Jiang et al. |
| 10,105,543 B2 | 10/2018 | Marnfeldt et al. |
| 10,118,040 B2 | 11/2018 | Zhu |
| 10,124,178 B2 | 11/2018 | Oron et al. |
| 10,143,845 B2 | 12/2018 | Kothandaraman |
| 10,149,976 B1 | 12/2018 | Andresen et al. |
| 10,173,062 B2 | 1/2019 | Parker |
| 10,177,609 B2 | 1/2019 | Olson et al. |
| 10,179,241 B2 | 1/2019 | Walker et al. |
| 10,182,807 B2 | 1/2019 | Bridgeman et al. |
| 10,195,425 B2 | 2/2019 | Ostroff et al. |
| 10,213,608 B2 | 2/2019 | Moffitt |
| 10,219,229 B1 | 2/2019 | Mulligan, IV |
| 10,226,637 B2 | 3/2019 | Aghassian et al. |
| 10,238,863 B2 | 3/2019 | Gross et al. |
| 10,449,374 B2 | 10/2019 | Oron et al. |
| 10,532,208 B2 | 1/2020 | Ostroff et al. |
| 10,583,284 B2 | 3/2020 | Peters et al. |
| 10,744,331 B2 | 8/2020 | Oron et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0014016 A1 | 1/2003 | Purdy |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0114905 A1 | 6/2003 | Kuzma |
| 2003/0176898 A1 | 9/2003 | Gross et al. |
| 2003/0236557 A1 | 12/2003 | Whitehurst et al. |
| 2003/0236558 A1 | 12/2003 | Whitehurst et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0254624 A1 | 6/2004 | Johnson |
| 2004/0153074 A1 | 8/2004 | Bojarski et al. |
| 2004/0167584 A1 | 8/2004 | Carroll et al. |
| 2004/0249431 A1 | 12/2004 | Ransbury et al. |
| 2004/0254612 A1 | 12/2004 | Ezra et al. |
| 2005/0113894 A1 | 5/2005 | Zilberman et al. |
| 2005/0131495 A1 | 6/2005 | Parramon et al. |
| 2005/0143789 A1 | 6/2005 | Whitehurst |

(56) References Cited

U.S. PATENT DOCUMENTS

| | | |
|---|---|---|
| 2005/0165457 A1 | 7/2005 | Benser et al. |
| 2005/0182457 A1 | 8/2005 | Throne et al. |
| 2005/0251061 A1 | 11/2005 | Schuler et al. |
| 2006/0085039 A1 | 4/2006 | Hastings et al. |
| 2006/0085042 A1 | 4/2006 | Hastings et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0088397 A1 | 4/2007 | Jacobson |
| 2007/0173893 A1 | 7/2007 | Pitts |
| 2007/0208392 A1 | 9/2007 | Kuschner et al. |
| 2007/0255369 A1 | 11/2007 | Bonde et al. |
| 2007/0293908 A1 | 12/2007 | Cowan et al. |
| 2007/0293912 A1 | 12/2007 | Cowan et al. |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0065182 A1 | 3/2008 | Strother et al. |
| 2008/0071178 A1 | 3/2008 | Greenland et al. |
| 2008/0091255 A1 | 4/2008 | Caparso et al. |
| 2008/0103407 A1 | 5/2008 | Bolea et al. |
| 2008/0103572 A1 | 5/2008 | Gerber |
| 2008/0109054 A1 | 5/2008 | Hastings et al. |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0043356 A1 | 2/2009 | Longhini et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0182402 A1 | 7/2009 | Glukhovsky |
| 2009/0204170 A1 | 8/2009 | Hastings et al. |
| 2009/0204173 A1 | 8/2009 | Fang et al. |
| 2009/0259280 A1 | 10/2009 | Wilkin et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1 | 1/2010 | Willis et al. |
| 2010/0049289 A1 | 2/2010 | Lund et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0280568 A1 | 11/2010 | Bulkes et al. |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0112605 A1 | 5/2011 | Fahey |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0224769 A1 | 9/2011 | Spenser et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0282412 A1 | 11/2011 | Glukhovsky et al. |
| 2011/0301670 A1 | 12/2011 | Gross |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0215285 A1 | 8/2012 | Tahmasian et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2013/0192611 A1 | 8/2013 | Taepke, II et al. |
| 2013/0325081 A1 | 12/2013 | Karst et al. |
| 2013/0325084 A1 | 12/2013 | Lee |
| 2014/0214134 A1 | 7/2014 | Peterson |
| 2014/0296940 A1 | 10/2014 | Gross |
| 2015/0004709 A1 | 1/2015 | Nazarpoor |
| 2015/0018598 A1 | 1/2015 | Nabutovsky et al. |
| 2015/0018728 A1* | 1/2015 | Gross ............... A61N 1/36167 601/46 |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0148878 A1 | 5/2015 | Yoo et al. |
| 2015/0174406 A1 | 6/2015 | Lamensdorf et al. |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0361544 A1 | 12/2016 | Oron et al. |
| 2017/0007829 A1 | 1/2017 | Gross |
| 2017/0119435 A1 | 5/2017 | Gross et al. |
| 2017/0128724 A1 | 5/2017 | Oron et al. |
| 2017/0136232 A1 | 5/2017 | Oron et al. |
| 2017/0224996 A1 | 8/2017 | Oron et al. |
| 2017/0232255 A1 | 8/2017 | Kent et al. |
| 2018/0126157 A1 | 5/2018 | Gross et al. |
| 2018/0140849 A1 | 5/2018 | Oron et al. |
| 2019/0070420 A1 | 3/2019 | Oron et al. |
| 2019/0217085 A1 | 7/2019 | Oron et al. |
| 2020/0046974 A1 | 2/2020 | Ostroff et al. |

FOREIGN PATENT DOCUMENTS

| | | |
|---|---|---|
| CN | 101947357 | 1/2011 |
| CN | 203154605 | 8/2013 |
| DE | 102008054403 | 6/2010 |
| EP | 0 688 577 | 12/1995 |
| EP | 1533000 | 5/2005 |
| EP | 1703638 | 11/2012 |
| EP | 3167930 | 2/2020 |
| WO | 1998/010832 | 3/1998 |
| WO | 1999/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 | 7/2013 |
| WO | 2013/111137 | 8/2013 |
| WO | 2013/156038 | 10/2013 |
| WO | 2013/164829 | 11/2013 |

(56) References Cited

FOREIGN PATENT DOCUMENTS

| WO | 2014/068577 A2 | 5/2014 |
|---|---|---|
| WO | 2014/068577 A3 | 5/2014 |
| WO | 2014/081978 | 5/2014 |
| WO | 2014/087337 | 6/2014 |
| WO | 2014/167568 | 10/2014 |
| WO | 2015/004673 | 1/2015 |
| WO | 2016/028608 | 2/2016 |
| WO | 2016/157183 | 10/2016 |
| WO | 2016/172109 | 10/2016 |

OTHER PUBLICATIONS

An Office Action dated Aug. 13, 2021, which issued during the prosecution of Chinese Patent Application No. 201610957461.7.
An Office Action dated Jun. 1, 2021, which issued during the prosecution of Chinese Patent Application No. 201610909174.9.
An Office Action dated Jun. 17, 2021, which issued during the prosecution of U.S. Appl. No. 16/363,256.
An Office Action dated May 6, 2021, which issued during the prosecution of Chinese Patent Application No. 201610957551.6.
An Office Action summarized English translation and Search Report dated May 6, 2021, which issued during the prosecution of Chinese Patent Application No. 201610957461.7.
C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4):322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 17, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. And Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M. Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.

(56) References Cited

OTHER PUBLICATIONS

Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013, which issued during the prosecution of Applicant's PCT/IL2013/050069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, ED M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
An Office Action dated May 19, 2017, which issued during the prosecution of U.S. Appl. No. 14/935,941.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
A Notice of Allowance dated Jun. 9, 2014, which issued during the prosecution of U.S. Appl. No. 12/796,102.
Notice of Allowance dated Sep. 1, 2017, which issued during the prosecution of U.S. Appl. No. 14/649,873.
Brindley (1983) A technique for modally blocking large nerve fibers.
An Office Action dated Sep. 22, 2016, which issued during the prosecution of U.S. Appl. No. 14/374,375.
DJOGlobal.com—Interferential Current Therapy (IFC).
A Notice of Allowance dated Apr. 25, 2014, which issued during the prosecution of U.S. Appl. No. 13/528,433.
An Office Action dated Sep. 26, 2013, which issued during the prosecution of U.S. Appl. No. 13/528,433.
U.S. Appl. No. 60/985,353, filed Nov. 5, 2007.
An Office Action dated Apr. 4, 2017, which issued during the prosecution of U.S. Appl. No. 14/601,604.
electrotherapy.org—Interferential Therapy.
An Office Action dated Feb. 27, 2017, which issued during the prosecution of U.S. Appl. No. 14/649,873.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European during the prosecution of Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Notice of Allowance dated Jun. 15, 2017, which issued during the prosecution of U.S. Appl. No. 14/939,418.
Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472.
UCLA Team Reports Initial Success with Trigeminal Nerve Stimulation epilepsy. https://web.archive.org/web/20121020145122/https://www.epilepsy.com/epilepsy/newsletter/apr09_STIM.
Kucklick, Theodore R., ed. *The medical device R&D handbook.* Chapter 3—Intro to needles and cannulae. CRC Press, 2012.
Szmurlo, R., Starzynski, J., Wincenciak, S. and Rysz, A. (2009) 'Numerical model of vagus nerve electrical stimulation', *COMPEL—The international journal for computation and mathematics in electrical and electronic engineering*, 28(1), pp. 211-220.
An Office Action dated Apr. 5, 2017, which issued during the prosecution of U.S. Appl. No. 14/374,375.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Reggiani et al. "Biophysical effects of high frequency electrical field on muscle fibers in culture." (2009) pp. 49-56.
An Office Action dated Aug. 8, 2016, which issued during the prosecution of U.S. Appl. No. 14/735,741.
An International Search Report and a Written Opinion both dated Jul. 11, 2013, which issued during the rosecution of Applicant's PCT/IL2013/050069.
An International Search Report and a Written Opinion both dated Apr. 29, 2014, whichissued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
An Office Action dated Dec. 12, 2016, which issued during the prosecution of U.S. Appl. No. 14/939,418.
Notice of Allowance dated Mar. 22, 2017, which issued during the prosecution of U.S. Appl. No. 14/939,418.
Injecta 2013 GmbH catalogue.

(56) References Cited

OTHER PUBLICATIONS

An Office Action dated Feb. 13, 2017, which issued during the prosecution of U.S. Appl. No. 14/601,604.
U.S. Appl. No. 61/733,995, filed Dec. 6, 2012.
Alo, Kenneth M., et al. "Lumbar and sacral nerve root stimulation (NRS) in the treatment of chronic pain: a novel anatomic approach and neuro stimulation technique." Neuromudulation: Technology at the Neural Interface 2.1 (1999): 23-31.
European Search Report dated Mar. 10, 2017, which issued during the prosecution of Applicant's European App No. 16196864.9.
An Office Action dated Nov. 21, 2016, which issued during the prosecution of U.S. Appl. No. 14/601,626.
Stuart, R. Morgan, and Christopher J. Winfree. "Neurostimulation techniques for painful peripheral nerve disorders." Neurosurgery Clinics of North America 20.1 (2009): 111-120.
European Search Report dated Feb. 3, 2017, which issued during the prosecution of Applicant's European App No. 16196878.9.
Gofeld, Michael, and John G. Hanlon. "Ultrasound-Guided Placement of a Paddle Lead Onto Peripheral Nerves: Surgical Anatomy and Methodology." Neuromodulation: Technology at the Neural Interface 17.1 (2014): 48-53.
An Office Action dated Dec. 6, 2017, which issued during the prosecution of U.S. Appl. No. 14/601,604.
An Office Action dated Dec. 26, 2017, which issued during the prosecution of U.S. Appl. No. 14/935,941.
An Office Action dated Jan. 8, 2018, which issued during the prosecution of U.S. Appl. No. 14/935,941.
An Office Action dated Mar. 5, 2018, which issued during the prosecution of U.S. Appl. No. 15/360,501.
An Office Action dated Nov. 30, 2017, which issued during the prosecution of U.S. Appl. No. 15/726,971.
A Notice of Allowance dated Feb. 15, 2018, which issued during the prosecution of U.S. Appl. No. 14/601,604.
A Notice of Allowance dated Jul. 16, 2018, which issued during the prosecution of U.S. Appl. No. 15/360,501.
An Office Action dated Jun. 4, 2018, which issued during the prosecution of U.S. Appl. No. 15/860,385.
Notice of Allowance dated Oct. 22, 2018, which issued during the prosecution of U.S. Appl. No. 15/860,385.
An Office Action dated Jun. 26, 2019, which issued during the prosecution of U.S. Appl. No. 15/395,257.
An Office Action dated Dec. 5, 2018, which issued during the prosecution of U.S. Appl. No. 15/581,390.
An Office Action dated Feb. 7, 2019, which issued during the prosecution of U.S. Appl. No. 15/706,956.
An Office Action dated Jul. 24, 2020, which issued during the prosecution of U.S. Appl. No. 16/363,256.
An Office Action dated Apr. 22, 2019, which issued during the prosecution of U.S. Appl. No. 15/638,924.
Notice of Allowance dated Jun. 17, 2019, which issued during the prosecution of U.S. Appl. No. 15/581,390.
Notice of Allowance dated May 20, 2020, which issued during the prosecution of U.S. Appl. No. 16/183,783.
An Interview Summary dated Sep. 6, 2018, which issued during the prosecution of U.S. Appl. No. 15/860,385.
An Office Action dated Dec. 21, 2020, which issued during the prosecution of U.S. Appl. No. 16/363,256.

\* cited by examiner

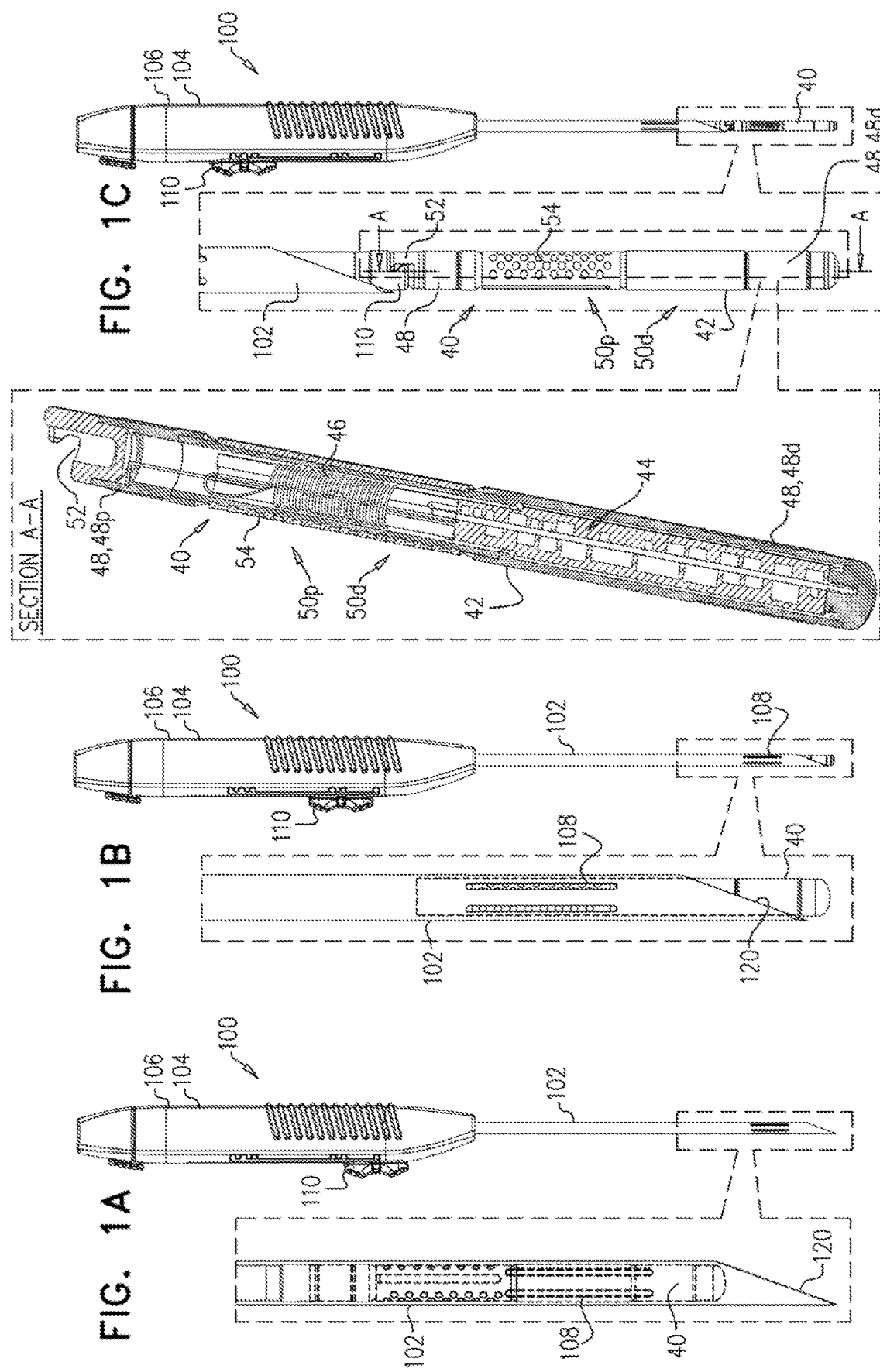

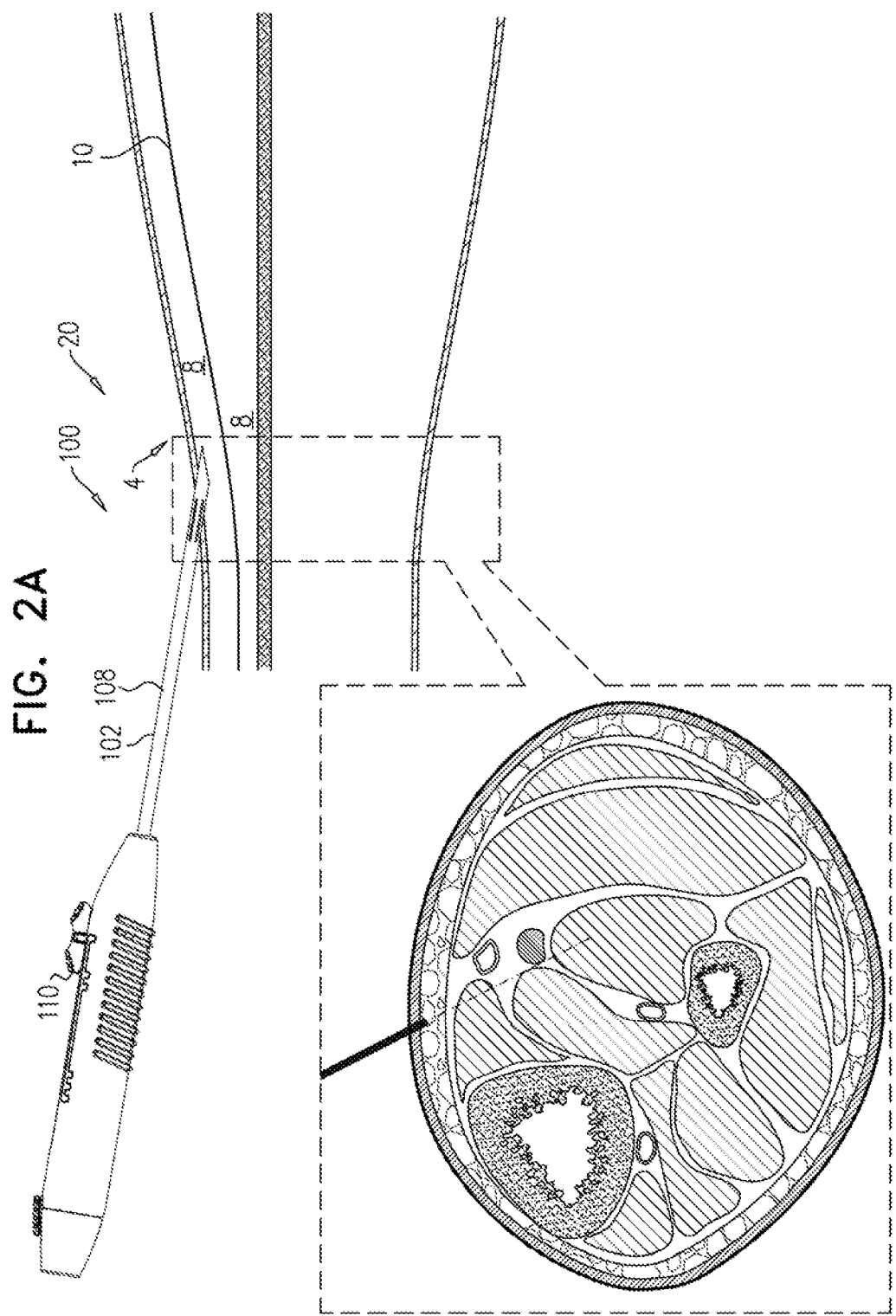

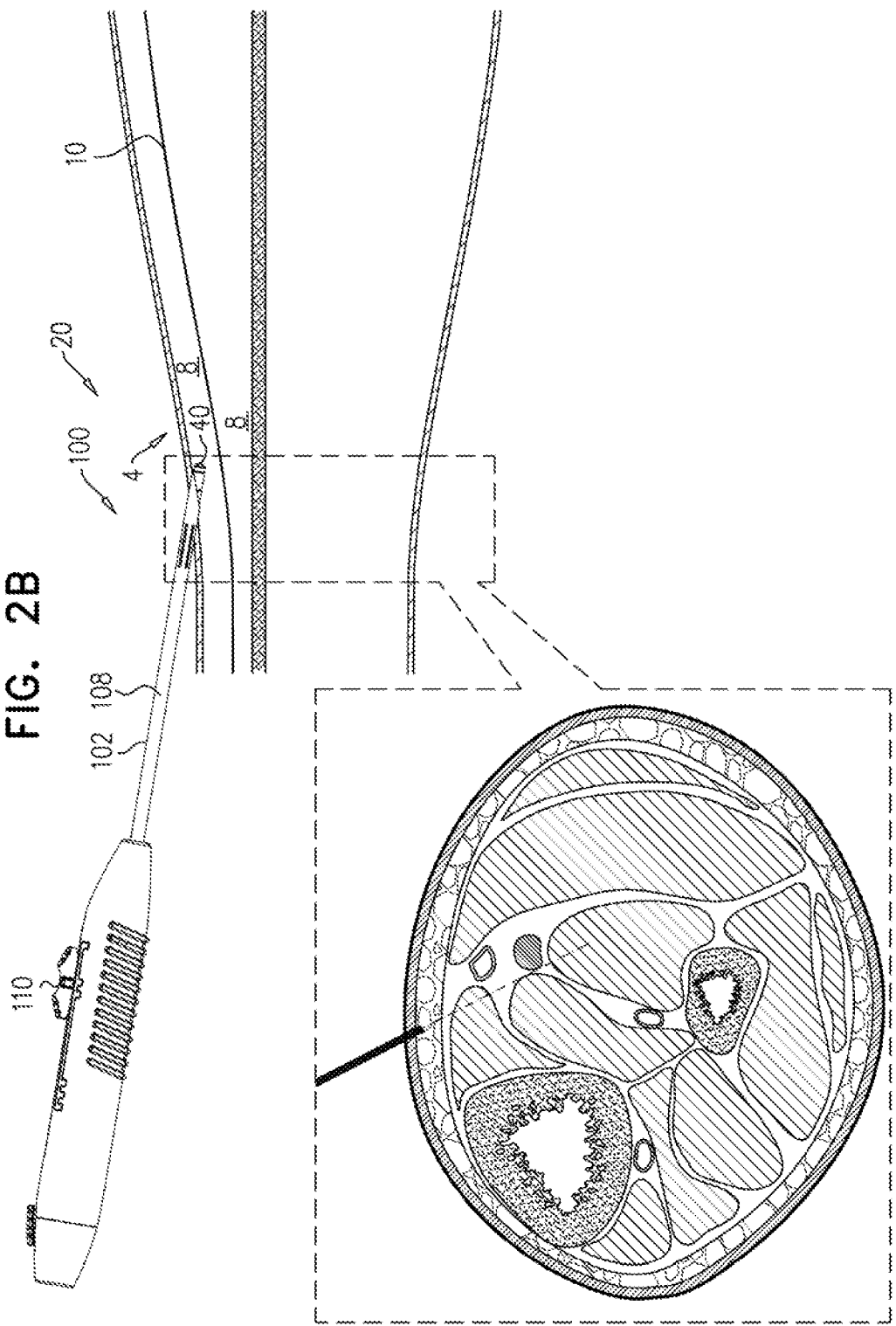

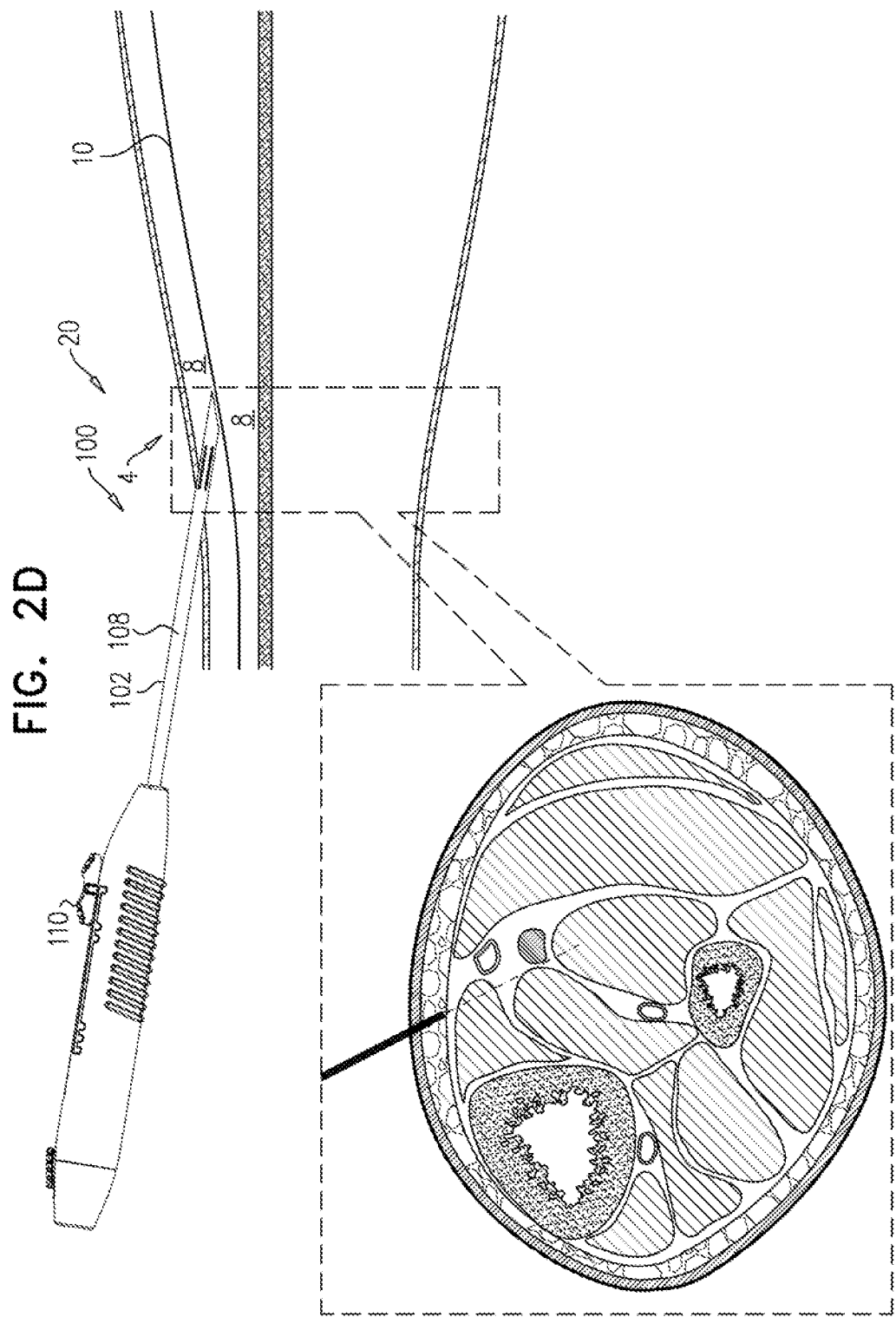

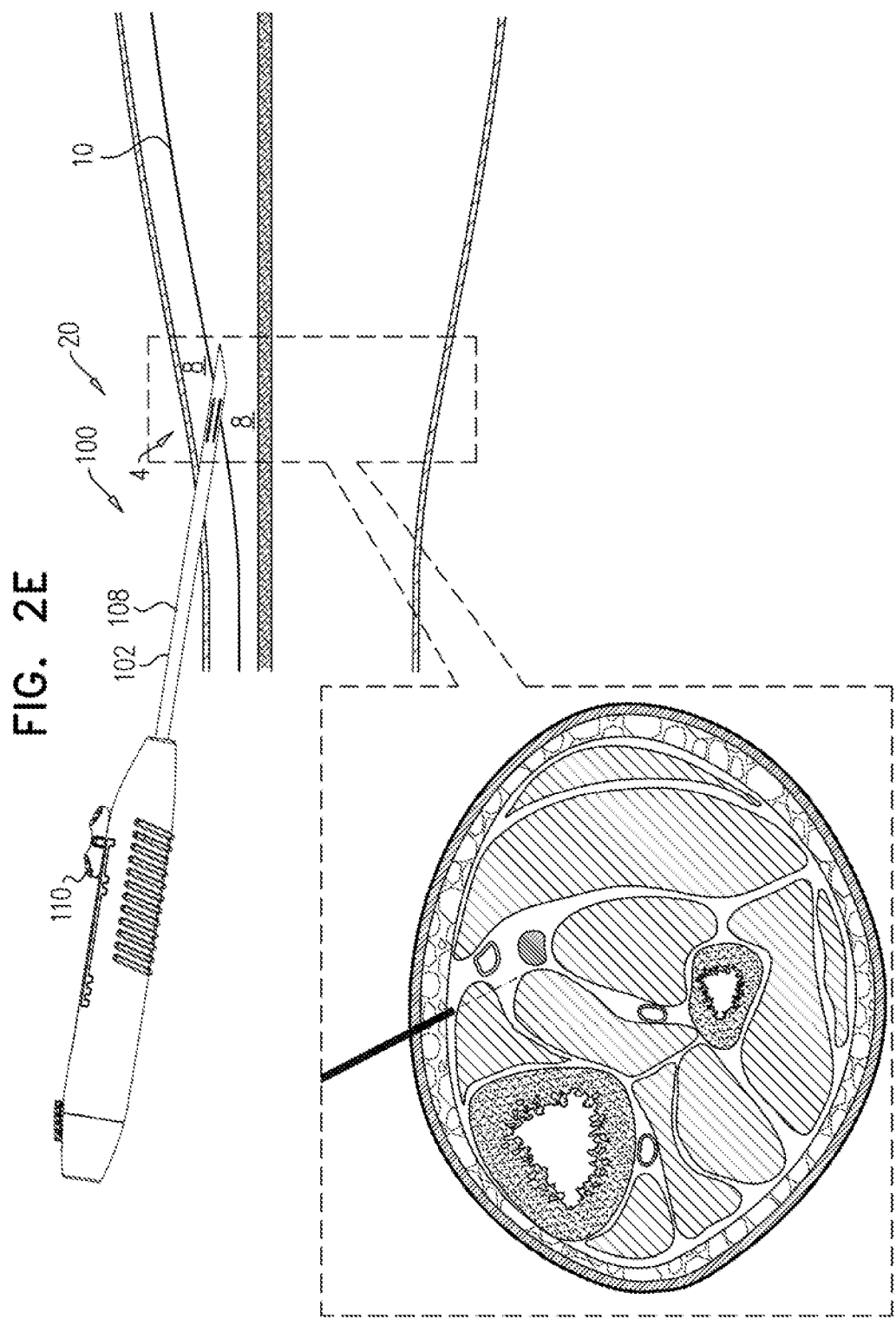

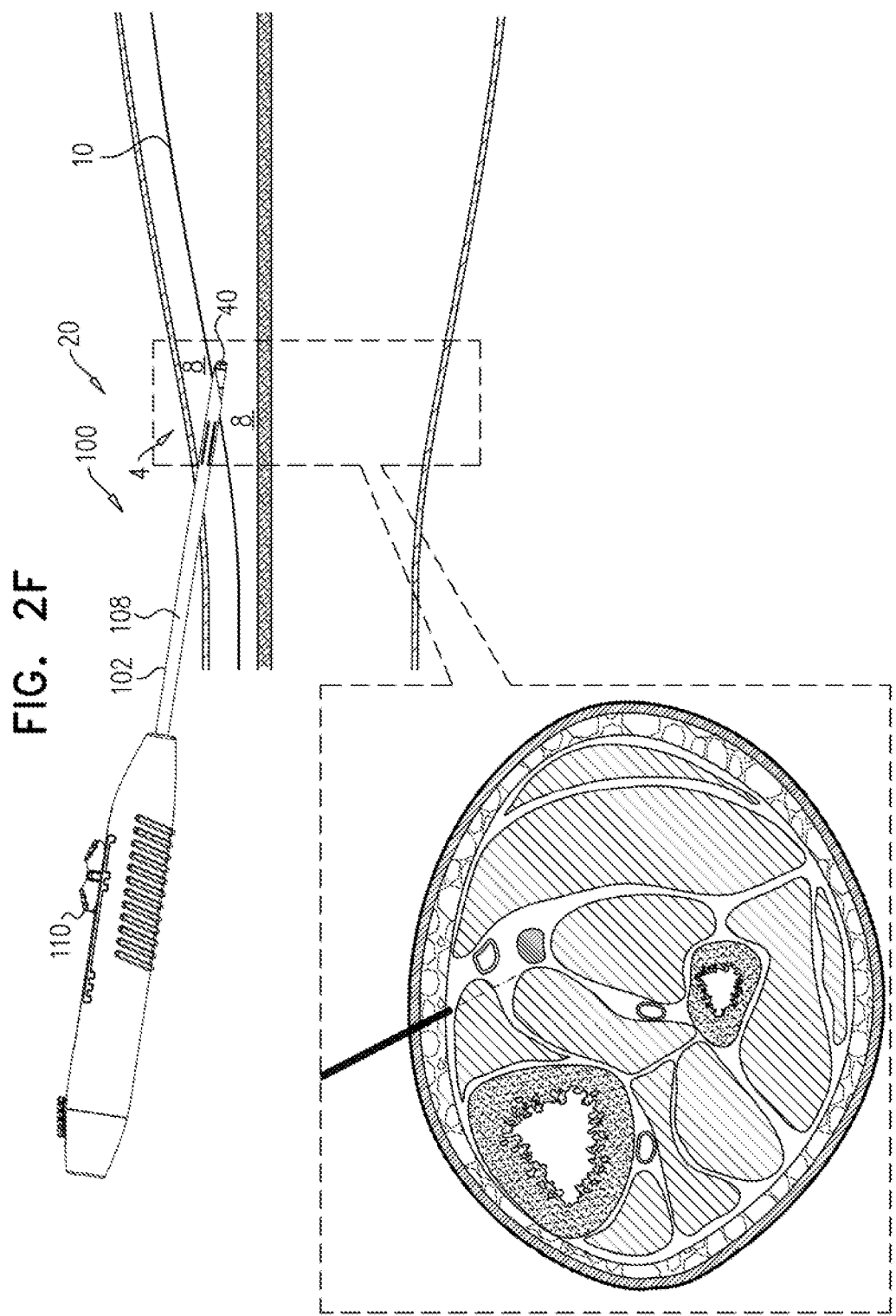

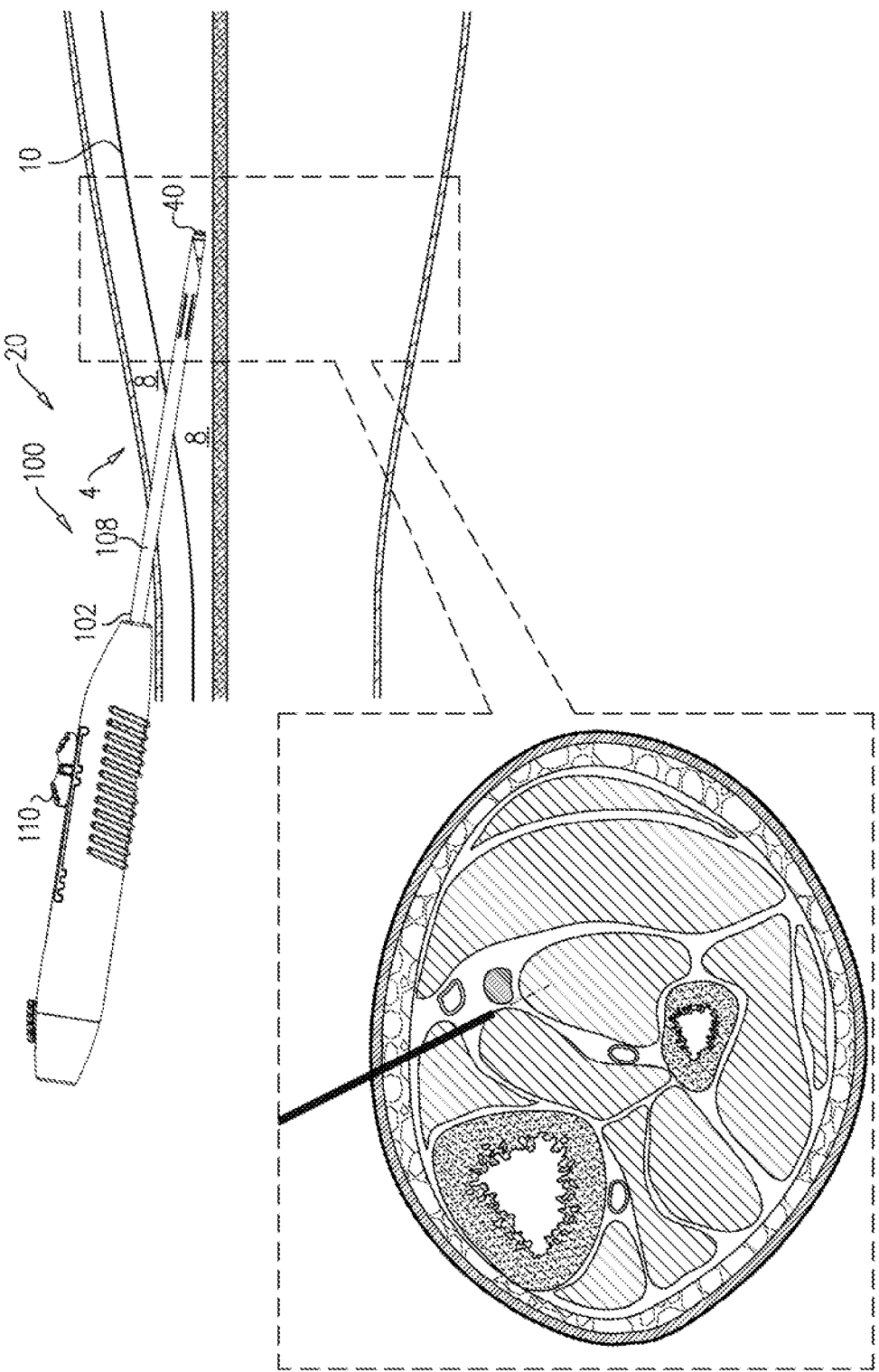

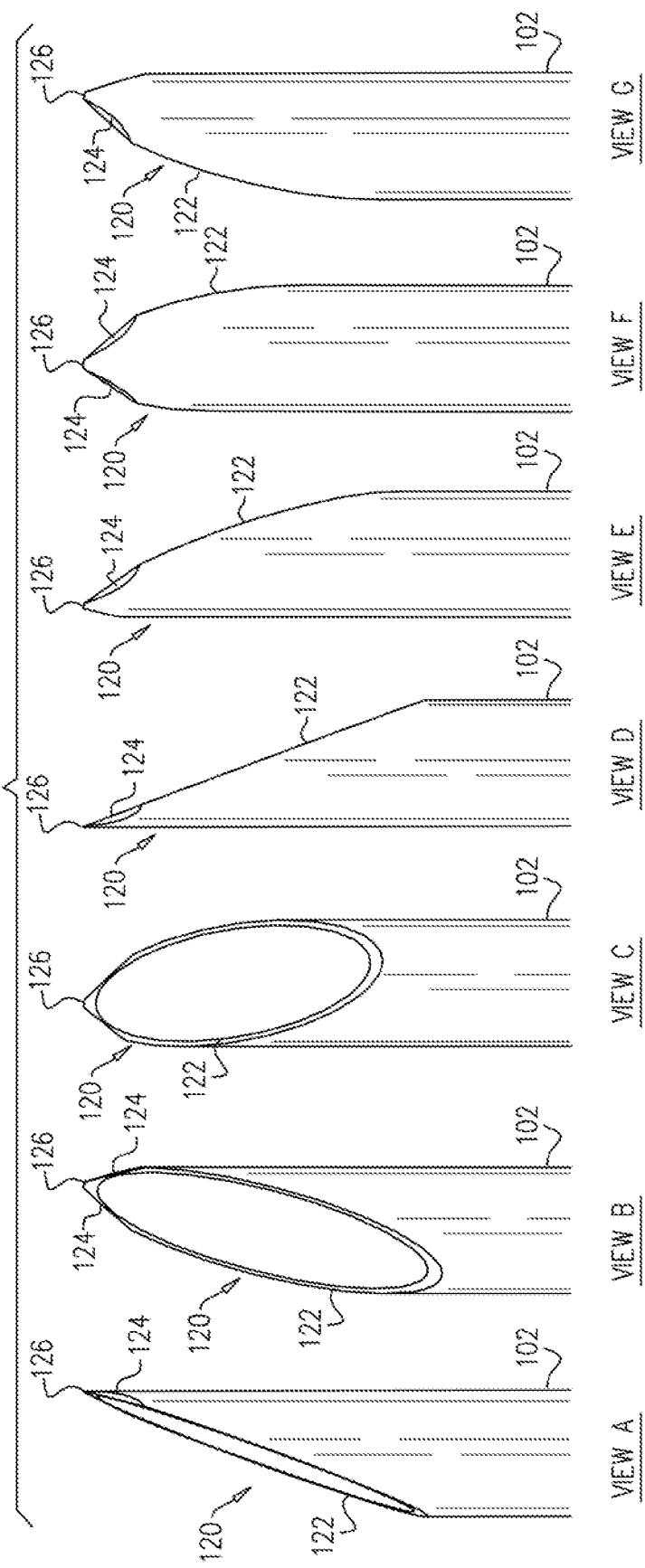

IMPLANT-DELIVERY TOOL

CROSS-REFERENCES TO RELATED APPLICATIONS

This patent application is a Continuation of U.S. Ser. No. 16/183,783 to Oron et al., filed Nov. 8, 2018, and entitled "Implant and delivery tool therefor," which issued as U.S. Pat. No. 10,744,331, and which is a Continuation of U.S. Ser. No. 15/360,501 to Oron et al., filed Nov. 23, 2016, and entitled "Implant and delivery tool therefor," which issued as U.S. Pat. No. 10,124,178.

FIELD OF THE INVENTION

The present invention relates generally to medical devices, and specifically to apparatus and methods for use with percutaneous implants.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Other disorders may cause pain to adjacent tissues.

Neurostimulation is a clinical tool used to treat various neurological disorders, and involves modulation of the nervous system by electrically activating fibers in the body.

SUMMARY OF THE INVENTION

For some applications of the invention, a system is provided comprising an implant, and a delivery tool therefor. The implant has an antenna and at least one electrode. The delivery tool comprises a hollow needle that typically has lateral openings. The delivery tool has discrete states. Typically, in a first state, the implant is entirely housed by the needle, and/or the antenna is disposed proximally from the lateral openings in the needle. Typically, in a second state, a distal portion of the implant is exposed out of the distal end of the needle, and/or the antenna is aligned with the lateral openings. In a third state, the implant is entirely disposed outside of the distal end of the needle. The system (i) facilitates testing of potential implantation sites for the implant, and (ii) increases the safety of advancing implants close to nerve tissue.

For some applications of the invention, the needle defines, at its distal end, a triple-grind bevel that defines (i) a primary grind, and (ii) two side-grinds that do not extend to meet each other to define a point at a distal-most part of the needle. This triple-grind bevel may be used for needles other than that of the delivery tool described herein.

For some applications, the implant defines a recessed portion around which a cuff is disposed, the cuff facilitating anchoring of the implant.

There is further provided, in accordance with an application of the present invention, apparatus for facilitating percutaneous delivery of an implant to a target site of a body of a subject, the implant including an antenna, and the apparatus including:

a delivery tool including a hollow needle that defines lateral openings in a wall of the needle, the hollow needle being configured to house the implant, the delivery tool being configured to define:

a first state, in which the implant is housed by the needle such that the antenna is disposed proximally from the lateral openings, a second state, in which a distal portion of the implant is exposed from a distal end of the needle, and the antenna is aligned with the lateral openings, and a third state, in which the implant is entirely disposed outside of the distal end of the needle.

In an application, in the first state, the entire implant is disposed within the needle.

In an application, in the first state, the entire implant is disposed proximally from the lateral openings.

In an application, in the first state, the distal portion of the implant is aligned with the lateral openings.

In an application, the hollow needle is a hollow metal needle.

In an application, the hollow needle defines a triple-grind bevel at the distal end of the needle, the triple-grind bevel defining:

a primary grind, and two side-grinds that do not extend to meet each other to define a point at a distal-most part of the needle.

In an application, the apparatus further includes the implant.

In an application:

the implant is an electrostimulator implant, and includes:

an implant body, the implant being injectable into tissue of a subject along a longitudinal axis of the implant body;

a proximal electrode, and a distal electrode disposed on the implant body distally from the proximal electrode, and in the second state of the delivery tool, the distal electrode is exposed from the distal end of the needle.

In an application, in the first state of the delivery tool, the proximal electrode and the distal electrode are disposed within the needle.

In an application, the antenna is configured to receive energy wirelessly.

There is further provided, in accordance with an application of the present invention, a method for percutaneously delivering an implant to a target site of a body of a subject, the method including:

inserting into tissue of the subject a hollow needle of a delivery tool, while the delivery tool is in a first state, in which the implant is entirely housed within the needle and no portion of the implant is exposed through the lateral openings in the needle wall;

subsequently, switching the delivery tool to a second state, in which a distal portion of the implant is exposed from a distal end of the needle, and a proximal portion of the implant is at least partially exposed through lateral openings defined by the needle wall; and subsequently, switching the delivery tool to a third state, in which the implant is entirely disposed outside of the distal end of the needle.

In an application, the method further includes, while the delivery tool is in the second state, advancing the delivery tool and the implant distally within the body of the subject.

There is further provided, in accordance with an application of the present invention, a method for percutaneously delivering an implant through a region of a body of the subject to a target site of the body, the region including a fascia and non-fascia tissue, the method including:

advancing, distally through the fascia, a hollow needle of a delivery tool, while the delivery tool is in a first state in which the implant is entirely housed within the needle;

switching the delivery tool to a second state in which a proximal portion of the implant is housed within the needle, and a distal portion of the implant is exposed from a distal end of the needle; and while the delivery tool is in the second state, advancing the hollow needle distally through non-fascia tissue.

In an application, the method further includes, prior to advancing the hollow needle distally through the fascia, switching the delivery tool into the first state.

In an application, the method further includes, prior to switching the tool into the first state, advancing the hollow needle distally through non-fascia tissue toward the fascia while the tool is in the second state.

In an application, the method further includes, subsequently to the step of advancing the hollow needle distally through the non-fascia tissue while the delivery tool is in the second state, switching the delivery tool to a third state, in which the implant is entirely disposed outside of the distal end of the needle.

In an application, the method further includes, while the delivery tool is in the third state, releasing the implant from the delivery tool.

There is further provided, in accordance with an application of the present invention, apparatus for facilitating percutaneous delivery of an implant to a target site of a body of a subject, the apparatus including:
a needle including:
a distal end; and
a proximal end,
the needle defining:
a lumen configured to facilitate passage of the implant therethrough, and
a triple-grind bevel at the distal end of the needle, the triple-grind bevel defining:
a primary grind, and
two side-grinds that do not extend to meet each other to define a point at a distal-most part of the needle.

In an application, the needle defines lateral openings in a wall of the needle, the openings being proximal from the distal end of the needle.

In application, the needle is a metal needle.

In an application, the two side-grinds converge distally at an angle of 65-85 degrees to each other.

In an application, the primary grind defines an angle of 15-25 degrees with respect to a central longitudinal axis of the needle.

In an application, the side-grinds converge distally, but at the distal-most part of the needle, the side-grinds are spaced apart by 0.1-0.4 mm.

There is further provided, in accordance with an application of the present invention, a method for percutaneously delivering an implant to a target site of a body of a subject, the method including:
inserting the implant into the subject's tissue;
activating the implant to apply a current to the subject's tissue at a first site within the tissue at a first power level;
measuring a response of the subject to the application of the current to the first site at the first power level;
in response to detecting that the subject responded in a given manner to the application of the current to the first site at the first power level, iteratively applying current to the first site at iteratively lower power levels until detecting that, at a second power level, the subject no longer responds, in the given manner, to the application of current to the first site; and
subsequently:

moving the implant to one or more further sites within the subject's tissue and applying current to the tissue, at the one or more further sites, at the second power level;
measuring a response of the subject to the application of current to the subject's tissue at the one or more further sites; and
in response to detecting that the subject responds, in the given manner, to application of the current at the second power level at a given one of the one or more further sites, implanting the implant closer to the given site than to the first site.

In an application:
inserting the implant includes inserting the implant while the implant is at least partly disposed within a hollow needle of a delivery tool,
moving the implant includes moving the implant while the implant is at least partly disposed within the hollow needle, and
activating the implant includes activating the implant while (i) the implant is at least partly disposed within the hollow needle, and (ii) an electrode of the implant is exposed from a distal end of the hollow needle.

In an application, activating the implant includes wirelessly activating the implant while an antenna of the implant is aligned with a lateral opening in a wall of the hollow needle.

In an application, moving the implant includes moving the implant while the electrode of the implant remains exposed from the distal end of the hollow needle.

There is further provided, in accordance with an application of the present invention, apparatus including:
an implant configured to be implanted in tissue of a subject, the implant including:
an implant body that includes:
at least a first longitudinal portion of the implant body that defines a given outer diameter; and
a recessed longitudinal portion of the implant body that is radially recessed with respect to the first longitudinal portion of the implant body, such that an outer diameter of the recessed longitudinal portion is less than the outer diameter of the first longitudinal portion; and
a cuff coupled to the implant body around the recessed longitudinal portion of the implant body such that an outer diameter of the cuff does not exceed the outer diameter of the first longitudinal portion,
the cuff defining a plurality of holes that are configured to facilitate anchoring of the implant body with respect to the subject's tissue, by facilitating tissue growth into the holes.

In an application, the cuff extends less than 360 degrees around the recessed longitudinal portion.

In an application, each hole of the plurality of holes has a diameter of 200-550 microns.

In an application, the cuff has a thickness of 200-550 microns.

In an application, the implant further includes an antenna, disposed within the recessed longitudinal portion.

In an application, the recessed longitudinal portion does not include a distal end or a proximal end of the implant.

In an application, the cuff includes a resilient material.

In an application, the apparatus further includes a delivery tool that includes a hollow needle through which the implant is slidable, and the outer diameter of the cuff is such that the cuff does not grip the inside of the hollow needle.

In an application, the hollow needle defines a triple-grind bevel at a distal end of the needle, the triple-grind bevel defining:
   a primary grind, and
   two side-grinds that do not extend to meet each other to define a point at a distal-most part of the needle.

The present invention will be more fully understood from the following detailed description of applications thereof, taken together with the drawings, in which:

BRIEF DESCRIPTION OF THE DRAWINGS

FIGS. 1A-C are schematic illustrations of a system comprising an implant and a delivery tool therefor, in accordance with some applications of the invention;

FIGS. 2A-H are schematic illustrations of a technique for using the delivery tool to implant the implant, in accordance with some applications of the invention;

FIGS. 3A-D are schematic illustrations of a tip of a needle of the delivery tool, in accordance with some applications of the invention.

DETAILED DESCRIPTION OF EMBODIMENTS

Figure 2C:
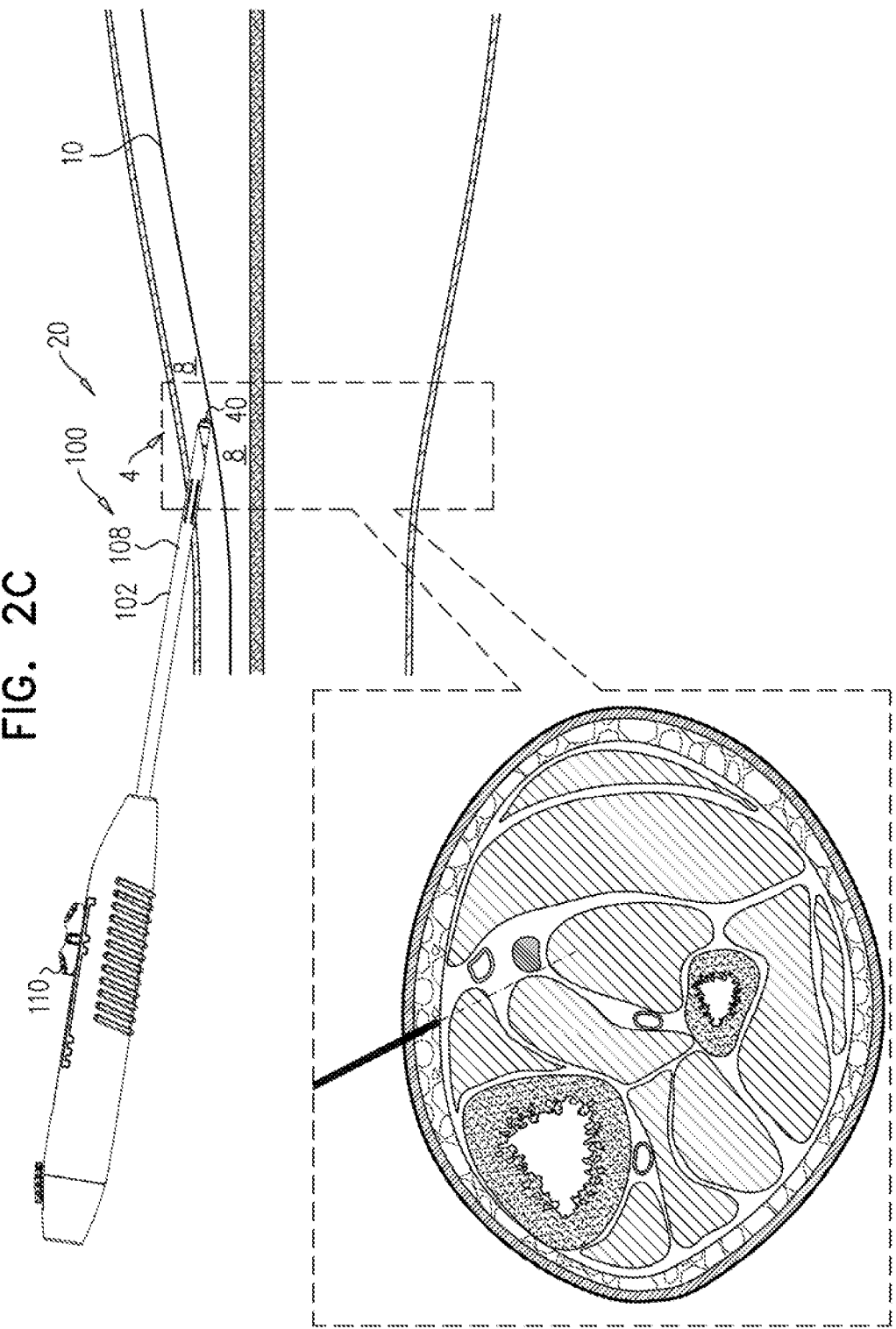

Reference is made to FIGS. 14-C, 2A-H, 3, and 4A-C, which are schematic illustrations of a system 20 and techniques for using the system, in accordance with some applications of the invention. System 20 comprises an implant 40, and a delivery tool 100 for percutaneous implantation of the implant.

Implant 40 comprises an implant body 42, circuitry 44 and an antenna 46 disposed within the implant body, and at least one electrode 48 (e.g., a proximal electrode 48p and a distal electrode 48d) disposed on the outside of the implant body. Implant 40 has a proximal portion 50p (e.g., a proximal half) that includes a proximal end of the implant, and a distal portion 50d (e.g., a distal half) that includes a distal end of the implant. Typically, at least one of electrodes 48 (e.g., a distal electrode 48d) is disposed at distal portion 50d. Typically, antenna 46 is disposed proximally from that at least one electrode 48. For example, antenna 46 may be disposed proximally from distal portion 50d, such as within proximal portion 50p.

At proximal portion 50p (e.g., at the proximal end) of implant 40, the implant (e.g., implant body 42) defines an implant-coupling 52 that is reversibly couplable to a complementary tool-coupling of tool 100.

Tool 100 comprises a hollow needle 102 at a distal part of the tool, and a control portion 104 at a proximal part of the tool, the control portion typically comprising a handle 106. Needle 102 has a lateral wall that circumscribes a longitudinal axis ax1 of the needle to define a lumen along the longitudinal axis. Needle 102 defines lateral openings 108 (e.g., longitudinal slits) in the lateral wall. Tool 100 is configured to define at least three states, which are shown in FIGS. 1-C, respectively.

FIGS. 1A-C show implant 40 loaded in tool 100. In the first state (FIG. 1A), implant 40 is housed by needle 102 such that antenna 46 is disposed proximally from openings 108. For some applications, in the first state the entire of implant 40 is disposed proximally from openings 108 (i.e., proximally along longitudinal axis ax1 of needle 102). Alternatively, and as shown, some of the implant (e.g., distal portion 50d) is aligned with openings 108 (i.e., disposed at the same part of longitudinal axis ax1 of needle 102), and/or distally from the openings (i.e., distally along the longitudinal axis of needle 102). Typically, and as shown, in the first state, all of electrodes 48 are disposed within needle 102 (i.e., the lumen thereof). For example, and as shown, in the first state, implant 40 may be disposed entirely within needle 102.

In the second state (FIG. 1B), distal portion 50d of implant 40 is exposed from the distal end of needle 102, and antenna 46 is aligned with openings 108 (i.e., disposed at the same part of longitudinal axis ax1 of the needle). Typically, in the second state, electrode 48d is exposed from the distal end of needle 102.

In the third state (FIG. 1C), implant 40 is entirely disposed outside of the distal end of needle 102.

Implant 40 is an electrostimulator implant, and drives electrodes 48 to apply current to tissue of the subject in which the implant is implanted. Implant 40 is controlled and/or powered wirelessly, e.g., by transmitting wireless signals from an extracorporeal controller (not shown). Such signals are received by antenna 46. Needle 102 is typically metallic. Openings 108 allow such wireless signals to pass into the lumen of needle 102. Other parts of needle 102 are relatively opaque to such signals. During implantation of implant 40, and before final deployment (i.e., release) of the implant, the implant is activated such that it drives electrodes 48 to apply current to the tissue, in order to determine if its current location within the tissue is an effective location for implanting the implant (e.g., by determining if its desired effect on the subject occurs). The inventors hypothesize that it is advantageous to prevent the operator (e.g., the physician) from inappropriately and/or inadvertently activating implant 40 (e.g., at an inappropriate time). In the first state, the wireless signals cannot reach (or cannot sufficiently reach) antenna 46. Therefore, the testing of the position of implant 40 cannot be performed in the first state. In the second state, the wireless signals can reach antenna 46, and therefore it is possible, in the second state, to test the position of implant 40. (Naturally, the wireless signals can reach antenna 46 also when tool 100 is in the third state, because in the third state implant 40 is entirely disposed outside of the distal end of needle 102.)

The use of openings 108 is particularly useful for applications in which the material from which needle 102 is formed is opaque to the wireless signals (e.g., a metal). For some applications, the material from which needle 102 is primarily formed may be transparent to the wireless signals (e.g., a polymer). For some such applications, needle 102 may have a metallic portion (e.g., a metallic shell radially inside, outside, or within the polymer, or as a distinct metallic longitudinal section between more proximal and distal polymer longitudinal sections), at the part of the needle at which antenna 46 is disposed in the first state of tool 100. The metallic portion inhibits the wireless signal from reaching (or sufficiently reaching) antenna 46, as described hereinabove, mutatis mutandis. Therefore, in a similar way to that described hereinabove, such a needle would also prevent inappropriate/inadvertent activation of implant 40 while tool 100 is in the first state, but would allow activation of the implant while the tool is in the second state. In a similar way, for some applications needle 102 may be primarily formed from a metal, but openings 108 are replaced by a polymer portion of the needle.

The embodiments described above have the following in common:
   The hollow needle has (i) a non-blocking longitudinal portion that allows the wireless signal to reach the antenna while the antenna is disposed in the non-blocking portion, and (ii) a blocking longitudinal portion that is significantly more opaque to the wireless signal than is the non-blocking portion, such that it blocks the wireless signal from activating the implant while the antenna is disposed in the blocking portion.

In the first state of the tool, the antenna is disposed in the blocking portion of the needle.

In the second state of the tool, the antenna is disposed in the non-blocking portion of the needle.

In the third state of the tool, the implant is entirely disposed outside of the distal end of the needle.

Typically, the non-blocking portion is closer than the blocking portion to the distal end of the needle.

For applications in which (i) in the first state all of electrodes 48 are disposed within needle 102, and (ii) in the second state electrode 48d is exposed from the distal end of the needle, the differing position of the electrodes between the first and second states may further prevent inappropriate and/or inadvertent driving of the current by implant 40. That is, in the first state, implant 40 cannot receive the wireless signals, and electrodes 48 are not exposed for application of current, whereas in the second state, implant 40 can receive the wireless signals, and t least one of electrodes 48 is exposed for application of current.

It is to be noted that, in the context of the first, second and third states of tool 100, the term "state" (including in the specification and the claims) means a discrete pre-configured condition of the tool, such as a condition in which the tool is configured to remain. Thus, tool 100 being configured to define the states means that tool 100 has particular features or elements that define the states and/or retain the tool in the states. For example, tool 100 (e.g., control portion 104) may comprise control elements 110 that enable switching between the states.

FIGS. 2A-H show steps in a technique for using tool 100 to implant implant 40 in a subject, in accordance with some applications of the invention. The example used is implantation of implant 40 close to a tibial nerve 6 of the subject, and in a distal to proximal direction, but the technique may be used at other anatomical sites and/or in other anatomical directions, mutatis mutandis. Each of FIGS. 2A-H shows a longitudinal cross-section and a transverse section of the lower leg 4 of a subject. The longitudinal cross-section illustrates the advancement of needle 102 through the tissue, and the state of tool 100. The transverse cross-section provides more anatomical detail, and schematically shows the depth to which needle 102 has penetrated. In the transverse cross-section, the element labeled 102 schematically represents needle 102. However, although in the transverse cross-section needle 102 should extend into and/or out of the page, a more simple representation is used for the sake of clarity.

Figure 2H:
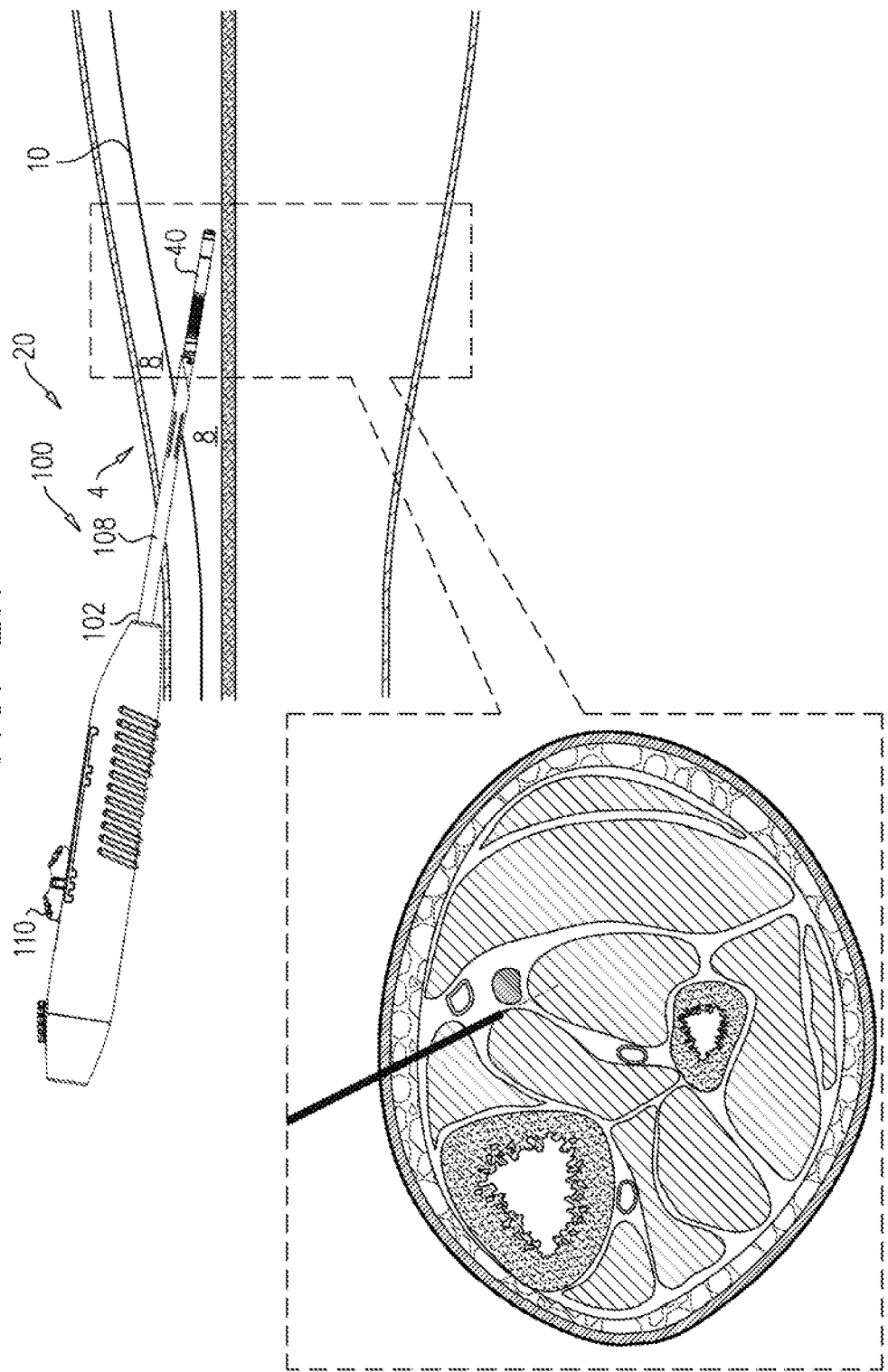

Needle 102 (e.g., a tip 120 thereof) is percutaneously advanced into the leg (FIG. 2A). For some applications, and as shown, needle 102 is advanced through the skin while tool 100 is in the first state, with tip 120 thereby defining the leading edge of system 20, e.g., such that needle 102 penetrates the skin. (Alternatively, an incision is made in the skin, and tool 100 is introduced via the incision, e.g., while in the second state). Subsequently, tool 100 is switched to the second state (FIG. 2B). Subsequently, and while tool 100 is in the second state, it is advanced through non-fascia tissue (e.g., fat tissue, and/or connective tissue) 8 of the leg, typically until reaching a fascia 10 (FIG. 2C). That is, system 20 is advanced through the non-fascia tissue with implant 40 distal to needle 102, and defining the leading edge of system 20. Upon reaching a fascia 10, tool 100 is switched to the first state (FIG. 2D), and advanced through the fascia while in the first state (FIG. 2E). Once through the fascia, the tool is switched to the second state (FIG. 2F), and advanced through more tissue 8 (FIG. 2G). As described hereinabove, in the second state it is possible to determine if the current location of implant 40 within the tissue is an effective location for implanting the implant. Once a suitable location of implant 40 is achieved (FIG. 2G), tool 100 is switched to the third state (FIG. 2H). Implant 40 is deployed (i.e., released from tool 100) at the suitable location, e.g., automatically upon tool 100 being switched to the third state, or as a result of a distinct subsequent deployment step.

As described hereinabove, determining that implant 40 is in a suitable location for implantation is achieved by activating the implant and, for example, detecting if the desired effect of the implant on the subject has occurred. It is hypothesized by the inventors that, for some applications, such a technique may be limited when the implant is activated to apply current at a single power level. For example, when a single power level is used, if an effect on the subject is detected when the implant is at a first site, and an effect on the subject is also detected when the implant is at a second site, the technique will not have provided information on which of the two sites is more suitable (e.g., closer to nerve 6). It is hypothesized by the inventors that such a technique may be improved by varying the power level at which implant 40 applies current to the tissue in which it is disposed. For example, if (1) after the effect is detected when the implant is at the first site, the implant is activated again, but using iteratively lower power levels until the effect is reduced (e.g., to below a threshold level, such as until the effect is not detected), and (2) when the lower power level is used at the second site, the effect is detected (and/or is above the threshold level), this indicates that the second site is more suitable (e.g., closer to nerve 6) than is the first site.

There is therefore provided, a method for percutaneously delivering an implant to a target site of a body of a subject, the method comprising:

(1) inserting the implant into the subject's tissue;

(2) activating the implant to apply a current to the subject's tissue at a first site within the tissue at a first power level;

(3) measuring a response of the subject to the application of the current to the first site at the first power level;

(4) in response to detecting that the subject responded in a given manner to the application of the current to the first site at the first power level, iteratively applying current to the first site at lower power levels, until detecting that, at a second power level, the subject no longer responds, in the given manner, to the application of current to the first site; and (5) subsequently:

(a) moving the implant to one or more further sites within the subject's tissue and applying current to the tissue, at the one or more further sites, at the second power level;

(b) measuring a response of the subject to the application of current to the subject's tissue at the one or more further sites; and (c) in response to detecting that the subject responds, in the given manner, to application of the current at the second power level at a given one of the one or more further sites, implanting the implant closer to the given site than to the first site.

For applications in which movement of the implant between the sites being tested does not require further penetration of a fascia, this movement of the implant between the sites is typically performed while the delivery tool remains in the second state.

Tip 120 is a beveled tip for penetrating tissue. It is hypothesized by the inventors that beveled tips are important for penetrating fascia 10 (and typically also skin 12), but that some other tissues (e.g., fat tissue and/or connective tissue) can be penetrated by implant 40 itself. Thus, in the technique shown in FIGS. 2A-H, implant 40 is advanced through tissue 8 while tool 100 is in the second state, thereby (as described hereinabove) facilitating identification of an effective location for implanting implant 40. It is further hypothesized by the inventors that as implant 40 becomes close to a target nerve such as tibial nerve 6, advancing the implant while tool 100 is in the second state reduces a likelihood of injuring the nerve or a nearby blood vessel with tip 120.

It is to be noted that the transition of tool 100 between its states is performed by retracting and advancing needle 102 with respect to control portion 104 (e.g., changing the effective length of the needle), rather than by advancing and retracting implant 40. This allows implant 40, once a suitable location has been identified, to be deployed from tool 100 without moving the implant with respect to the surrounding tissue (FIGS. 2G-H).

FIGS. 3A-D show detailed views of tip 120 of needle 102 of tool 100, in accordance with some applications of the invention. Tip 120 has a triple-grind bevel that defines a primary grind 122 (alternatively termed a primary bevel) and two side-grinds 124 (alternatively termed secondary bevels, or lancets). Unlike other triple-grind needles, side-grinds 124 do not extend to meet each other to define a point (i.e., a distal point) at a distal-most part of needle 102 (i.e., at the very tip of the needle). That is, primary grind 122 contributes to the pointedness of the distalmost part 126 of tip 120, but side-grinds 124 do not. Thus, part 126 appears pointed when tip 120 is viewed from the side (e.g., when viewed such that primary grind 122 forms part of the outline of the tip) (e.g., FIG. 3A view D), but appears blunt or rounded when the tip is viewed from above or below (e.g., when viewed such that side-grinds 124 are both visible) (e.g., FIG. 3A views C and F, and FIG. 3B). Therefore, side-grinds 124 converge toward distalmost part 126, but even where they are closest to each other (i.e., at or near to part 126), they are spaced apart by a distance d5.

For some applications, primary grind 122 defines an angle of 15-25 (e.g., 18-22, such as 20) degrees with respect to the lateral wall and/or central longitudinal axis ax1 of needle 102. For some applications, side-grinds 124 converge distally at an angle alpha_1 of 65-85 (e.g., 74-78, such as 76) degrees to each other (see FIG. 3B). For some applications, distance d5 is 0.1-0.4 mm (e.g., 0.16-0.28 mm, such as 0.22 mm).

Figure 3B:
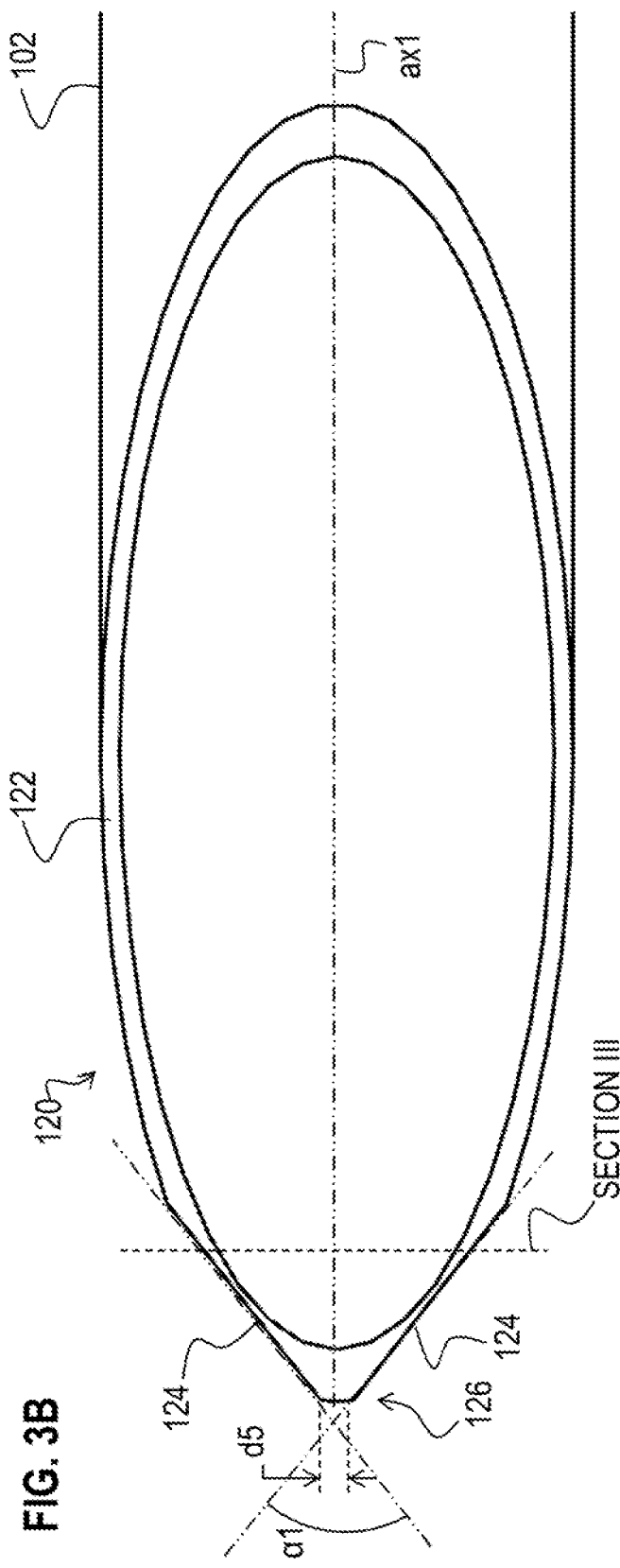
Figure 3D:
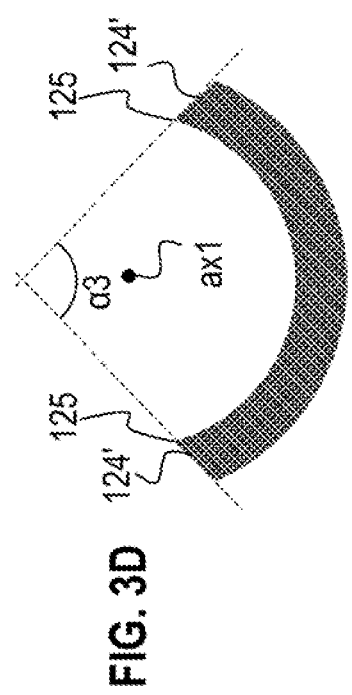
Figure 3C:
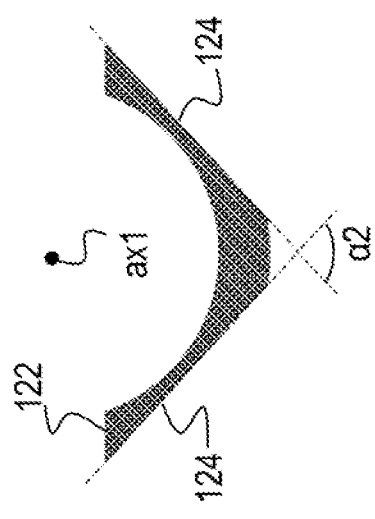

FIG. 3C shows a transverse cross-section of tip 120 at section III (shown in FIG. 3B), according to some applications of the invention. For such applications, side-grinds 124 face away from primary grind 122. That is, side-grinds 124 are "underneath" the needle, and do not eliminate the sloped surface of primary grind 122. Hence the surface of primary grind 122 is visible in FIG. 3C, In transverse cross-section, the planes of side-grinds 124 are disposed at an angle alpha_2 that is typically 100-150 (e.g., 110-140, e.g., 120-140, such as 130) degrees with respect to each other. For some applications, this is similar to a "back bevel point" needle tip, but without the side-grinds extending to meet each other to define a point at the distal-most part of the needle. Therefore, angle alpha_2 may be described as a back bevel angle.

FIG. 3D shows a transverse cross-section of tip 120, according to some alternative applications of the invention. For such applications, side-grinds 124' face toward primary grind 122. That is, side-grinds 124' are on the same side of the needle as primary grind 122, and at the longitudinal portion of the needle at which they are disposed, they eliminate the sloped surface of primary grind 122, leaving a ridge 125. In transverse cross-section, the planes of side-grinds 124' are disposed at an angle alpha_3 with respect to each other. For some applications, this is similar to a "lancet point" needle tip, but without the side-grinds extending to meet each other to define a point at the distal-most part of the needle. Therefore, angle alpha_3 may be described as a lancet angle.

There is therefore provided, in accordance with some applications of the invention, apparatus for facilitating percutaneous delivery of an implant to a target site of a body of a subject, the apparatus comprising a needle that (1) comprises (a) a distal end; and (b) a proximal end, and (2) defines: (a) a lumen configured to facilitate passage of the implant therethrough, and (b) a triple-grind bevel at the distal end of the needle, the triple-grind bevel defining: (i) a primary grind, and (ii) two side-grinds that do not extend to meet each other to define a point at a distal-most part of the needle.

It is hypothesized by the inventors that tip 120 advantageously has both (i) the tissue-penetrating benefits of existing triple-grind needles, and (ii) a distalmost part that is relatively rounded and less likely to injure a target nerve or an adjacent blood vessel, compared to such existing triple-grind needles.

Figure 4C:
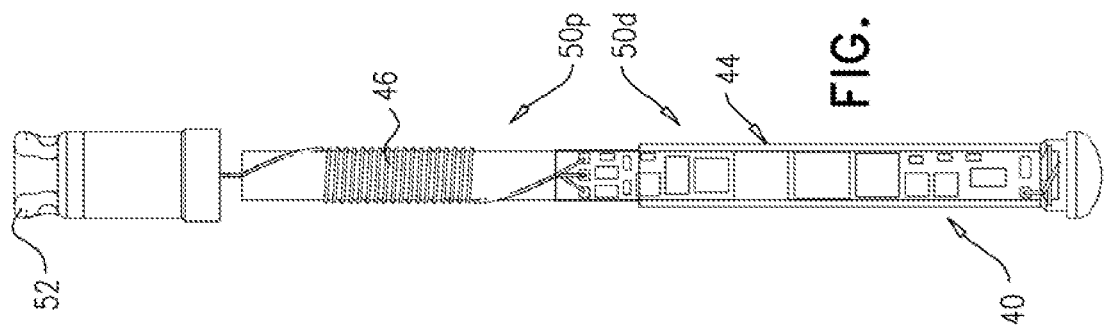
FIGS. 4A-C are schematic illustrations of the implant, in accordance with some applications of the invention.
Figure 4B:
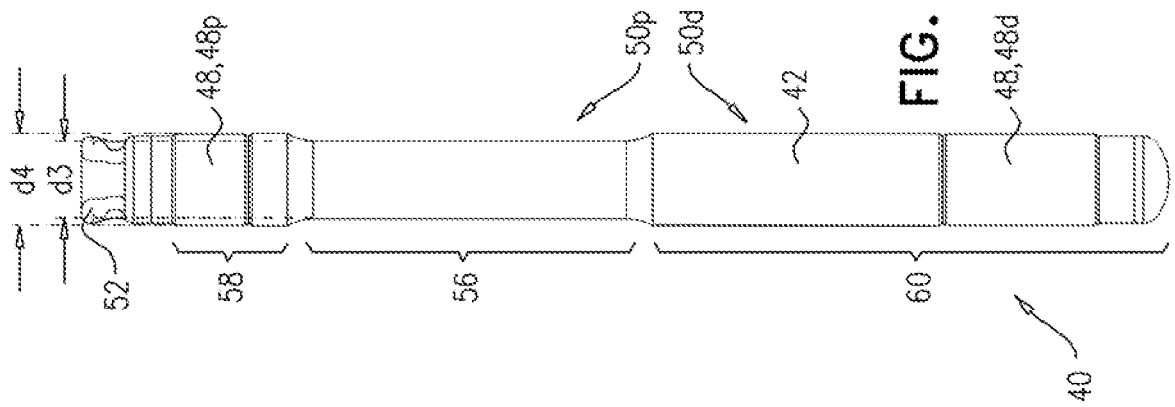
Figure 4A:
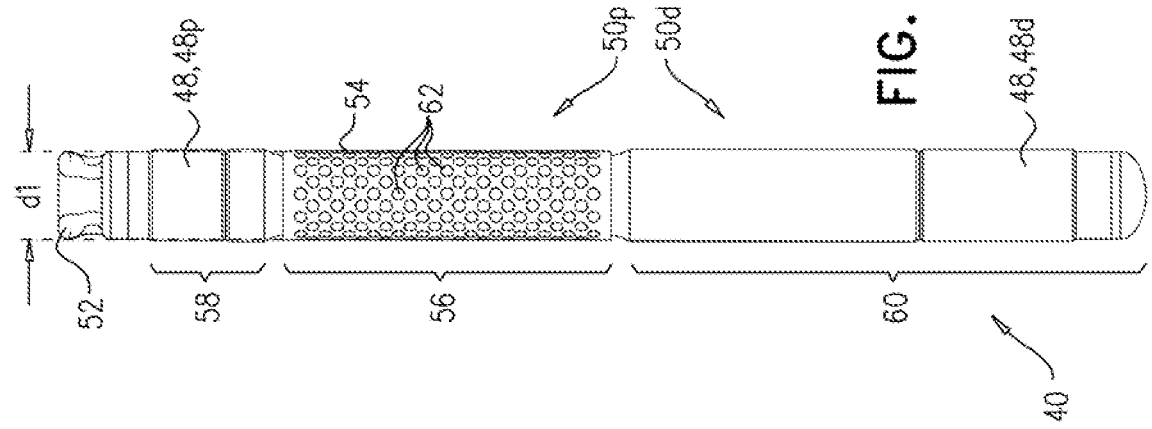

FIGS. 4A-C show respective views of implant 40. FIG. 4A shows implant 40 in its entirety. As described hereinabove, circuitry 44 and antenna 46 are disposed within implant body 42, and the at least one electrode 48 is disposed on the outside of the implant body. Also as described hereinabove, at least one of electrodes 48 (e.g., distal electrode 48d) is disposed at distal portion 50d. Typically, another electrode (e.g., proximal electrode 48p) is disposed at proximal portion 50p. Antenna 46 is typically disposed proximally from electrode 48d (e.g., within proximal portion 50p).

Implant 40 comprises a cuff 54, which circumscribes a recessed longitudinal portion 56 of implant body 42. FIG. 4B illustrates implant 40 with cuff 54 removed, thereby showing recessed longitudinal portion 56. In the example shown, recessed longitudinal portion 56 is defined by at least part of proximal portion 50p. However, recessed longitudinal portion 56 may alternatively or additionally be defined by at least part of distal portion 50d.

Recessed longitudinal portion 56 is radially recessed with respect to at least one other longitudinal portion of the implant body, such that an outer diameter of the recessed longitudinal portion is less than the outer diameter of the other longitudinal portion. In the example shown, the other longitudinal portion may be a longitudinal portion 58 proximal to portion 56 (e.g., another part of proximal portion 50p), or a longitudinal portion 60 distal to portion 56 (e.g., part of distal portion 50d). For example, an outer diameter d3 of recessed longitudinal portion 56 is less than an outer diameter d4 of portion 58, and is also less than an outer diameter of portion 60 (which may be the same as diameter d4), and therefore does not include the distal end or the proximal end of the implant.

Cuff 54 is configured to be coupled to implant body 42 by being coupled to (e.g., wrapped around) recessed longitudinal portion 56 such that, when the cuff is coupled to portion 56, an outer diameter d1 of the cuff does not exceed diameter d4. For some applications, cuff 54 extends less than 360 degrees (e.g., 340-355 degrees) around implant body 42. Typically, cuff 54 has a thickness of 100-500 (e.g., 200-250, such as 225) microns.

Cuff 54 defines a plurality of holes 62. Each hole 62 may have a diameter of 200-550 (e.g., 280-340) microns. Cuff 54 typically comprises a resilient material. For some applications, cuff 54 comprises polyether ether ketone, polyethylene terephthalate, fluorinated ethylene propylene, polyimide, acrylic, nylon, polytetrafluoroethylene, or polyetherimide (e.g., Ultem). This material and/or holes 62 increase the resistance of cuff 54, and therefore implant 40, to movement once implanted in tissue (e.g., the cuff grips the tissue). That is, cuff 54 serves as an anchor. Because diameter d1 does not exceed diameter d4, cuff 54 does not grip the inside of needle 102 (i.e., does not increase friction of the implant against the inside of the needle), and thereby does not interfere with movement of implant 40 within the needle during delivery and deployment of the implant. Holes 62 are further configured to facilitate anchoring of implant 40 with respect to the tissue, by facilitating tissue growth into the holes.

FIG. 4C shows implant 40 with electrodes 48 and most of implant body 42 removed, thereby showing antenna 46 and circuitry 44. For some applications, and as shown, antenna 46 is disposed in recessed longitudinal portion 56.

It is to be noted that for some applications tool 100 may be used to deliver implants other than implant 40. For example, tool 100 may be used to deliver a different electrostimulator implant, or an implant that is not an electrostimulator implant. It is to be further noted that, for some applications, needle 102 (e.g., tip 120 thereof) may be used in delivery tools other than tool 100. It is to be further noted that needle 102 may be useful for applications other than percutaneous implantation of an implant.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for facilitating percutaneous delivery of an implant to a target site of a body of a subject, the apparatus comprising a delivery tool, the delivery tool comprising a needle, the needle comprising:
a distal end; and
a proximal end,
the needle defining:
a lumen configured to facilitate passage of the implant therethrough,
lateral openings in a wall of the needle, the openings being proximal from the distal end of the needle, and
a triple-grind bevel at the distal end of the needle, the triple-grind bevel defining:
a primary grind, and
two side-grinds that do not extend to meet each other to define a point at a distal-most part of the needle.

2. The apparatus according to claim 1, wherein the two side-grinds converge distally at an angle of 65-85 degrees to each other.

3. A system comprising the apparatus according to claim 1, further comprising the implant.

4. The apparatus according to claim 1, wherein the side-grinds converge distally, but at the distal-most part of the needle, the side-grinds are spaced apart by 0.1-0.4 mm.

5. A system comprising the apparatus according to claim 1, the system further comprising the implant, the implant comprising an antenna, and
the delivery tool being configured to define:
a first state, in which the implant is housed within the lumen of the needle such that the antenna is disposed proximally from the lateral openings,
a second state, in which a distal portion of the implant is exposed from a distal end of the needle, and the antenna is aligned with the lateral openings, and
a third state, in which the implant is entirely disposed outside of the distal end of the needle.

6. The system according to claim 5, wherein in the first state, the entire implant is disposed within the needle.

7. The system according to claim 5, wherein in the first state, the entire implant is disposed proximally from the lateral openings.

8. The system according to claim 5, wherein in the first state, the distal portion of the implant is aligned with the lateral openings.

9. The system according to claim 5, wherein:
the implant is an electrostimulator implant, and comprises:
an implant body, the implant being injectable into tissue of the subject along a longitudinal axis of the implant body, the antenna disposed within the implant body;
a proximal electrode disposed on the implant body, and
a distal electrode disposed on the implant body distally from the proximal electrode, and
in the second state of the delivery tool, the distal electrode is exposed from the distal end of the needle.

10. The system according to claim 9, wherein in the first state of the delivery tool, the proximal electrode and the distal electrode are disposed within the needle.

11. The system according to claim 9, wherein:
the implant body has a recessed longitudinal portion that is radially recessed with respect to another longitudinal portion of the implant body, such that an outer diameter of the recessed longitudinal portion is less than the outer diameter of the other longitudinal portion,
the antenna is disposed in the recessed longitudinal portion, and
the distal electrode is disposed on the other longitudinal portion.

12. The system according to claim 11, wherein the recessed longitudinal portion is configured to facilitate reception of a wireless signal, by the antenna, while the delivery tool is in the second state and while the delivery tool is in the third state.

13. The system according to claim 5, wherein the antenna is configured to receive energy wirelessly.

14. Apparatus for facilitating percutaneous delivery of an implant to a target site of a body of a subject, the apparatus comprising a delivery tool, the delivery tool comprising a needle, the needle comprising:
a distal end; and
a proximal end,
the needle defining:
a lumen configured to facilitate passage of the implant therethrough, and
a triple-grind bevel at the distal end of the needle, the triple-grind bevel defining:
a primary grind, and two side-grinds that converge distally, but at the distal-most part of the needle, are spaced apart by 0.1-0.4 mm.

15. A system comprising the apparatus according to claim 14, the system further comprising the implant, the implant comprising an antenna, wherein:
the needle defines lateral openings in a wall of the needle, the openings being proximal from the distal end of the needle; and
the delivery tool is configured to define:
a first state, in which the implant is housed within the lumen of the needle such that the antenna is disposed proximally from the lateral openings,
a second state, in which a distal portion of the implant is exposed from a distal end of the needle, and the antenna is aligned with the lateral openings, and
a third state, in which the implant is entirely disposed outside of the distal end of the needle.

16. The system according to claim 15, wherein in the first state, the entire implant is disposed within the needle.

17. The system according to claim 15, wherein in the first state, the entire implant is disposed proximally from the lateral openings.

18. The system according to claim 15, wherein in the first state, the distal portion of the implant is aligned with the lateral openings.

19. Apparatus for facilitating percutaneous delivery of an implant to a target site of a body of a subject, the apparatus comprising a delivery tool, the delivery tool comprising a needle, the needle comprising:
a distal end; and
a proximal end,
the needle defining:
a lumen configured to facilitate passage of the implant therethrough, and
a triple-grind bevel at the distal end of the needle, the triple-grind bevel defining:
a primary grind, and
two side-grinds that:
converge distally at an angle of 65-85 degrees to each other, and
do not extend to meet each other to define a point at a distal-most part of the needle.

20. A system comprising the apparatus according to claim 19, the system further comprising the implant, the implant comprising an antenna, wherein:
the needle defines lateral openings in a wall of the needle, the openings being proximal from the distal end of the needle; and
the delivery tool is configured to define:
a first state, in which the implant is housed within the lumen of the needle such that the antenna is disposed proximally from the lateral openings,
a second state, in which a distal portion of the implant is exposed from a distal end of the needle, and the antenna is aligned with the lateral openings, and
a third state, in which the implant is entirely disposed outside of the distal end of the needle.

* * * * *